US011572396B2

(12) United States Patent
Morrell et al.

(10) Patent No.: US 11,572,396 B2
(45) Date of Patent: Feb. 7, 2023

(54) THERAPEUTIC USE OF BONE MORPHOGENETIC PROTEINS

(71) Applicant: CAMBRIDGE ENTERPRISE LIMITED, Cambridge (GB)

(72) Inventors: Nicholas W. Morrell, Cambridge (GB); Wei Li, Cambridge (GB); Paul D Upton, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 244 days.

(21) Appl. No.: 16/415,006

(22) Filed: May 17, 2019

(65) Prior Publication Data

US 2019/0359668 A1  Nov. 28, 2019

Related U.S. Application Data

(63) Continuation of application No. 15/324,864, filed as application No. PCT/GB2015/051989 on Jul. 9, 2015, now Pat. No. 10,336,800.

(30) Foreign Application Priority Data

Jul. 10, 2014 (GB) ..................................... 1412290

(51) Int. Cl.
*A61K 38/18* (2006.01)
*A61K 38/00* (2006.01)
*C07K 14/51* (2006.01)
*A61K 48/00* (2006.01)

(52) U.S. Cl.
CPC .............. *C07K 14/51* (2013.01); *A61K 38/18* (2013.01); *A61K 38/1875* (2013.01); *A61K 38/00* (2013.01); *A61K 48/00* (2013.01)

(58) Field of Classification Search
None
See application file for complete search history.

(56) References Cited

U.S. PATENT DOCUMENTS

| | | | |
|---|---|---|---|
| 5,288,931 A | 2/1994 | Chang et al. | |
| 7,112,660 B1 | 9/2006 | Domingues et al. | |
| 2003/0045474 A1 | 3/2003 | Sailer et al. | |
| 2006/0024783 A1 | 2/2006 | Seehra et al. | |
| 2013/0281371 A1 | 10/2013 | Kumar et al. | |
| 2014/0154743 A1 | 6/2014 | Levy et al. | |
| 2017/0209540 A1 | 7/2017 | Morrell et al. | |
| 2018/0050089 A1 | 2/2018 | Kumar et al. | |
| 2019/0359668 A1* | 11/2019 | Morrell ..................... | A61P 9/12 |

FOREIGN PATENT DOCUMENTS

| | | |
|---|---|---|
| CN | 101652387 A | 2/2010 |
| CN | 107760779 A | 3/2018 |
| EP | 1 571 159 A1 | 9/2005 |
| EP | 2 265 603 B1 | 12/2010 |
| JP | 2018-70625 A | 5/2018 |
| WO | 93/00432 A1 | 1/1993 |
| WO | 94/26893 A1 | 11/1994 |
| WO | 95/24474 A1 | 9/1995 |
| WO | 95/33830 A1 | 12/1995 |
| WO | 96/39431 A1 | 12/1996 |
| WO | 2005/113590 A2 | 12/2005 |
| WO | 2006/130022 A1 | 12/2006 |
| WO | 2008/014054 A2 | 1/2008 |
| WO | 2008/057461 A2 | 5/2008 |
| WO | 2008/151078 A1 | 12/2008 |
| WO | 2009/114180 A1 | 9/2009 |
| WO | 2010/114833 A1 | 10/2010 |
| WO | 2010/115874 A1 | 10/2010 |
| WO | 2012/145539 A1 | 10/2012 |
| WO | 2013/152213 A1 | 10/2013 |
| WO | 2014/160203 A2 | 10/2014 |
| WO | 2022/035260 A1 | 2/2022 |

OTHER PUBLICATIONS

Long et al. (2015, Nature Medicine 21:777-785).*
Tu et al. (2019, Circ. Res. 124:846-855).*
Ormiston et al. (2019, Circ. Res. 124:822-824).*
Morrell et al. (2019, Circ. Res. 124:e81).*
Guignabert et al. (2019, Circ. Res. 124:e82-e83).*
Justice et al. Using the mouse to model human disease: increasing validity and reproducibility. Disease, Models & Mechanisms 9: 101-103, 2016.*
Atkinson C. et al., "Primary Pulmonary Hypertension is Associated With Reduced Pulmonary Vascular Expression of Type II Bone Morphogenetic Protein Receptor", Circulation 105:1672-1678 (2002).
Bidart M. et al., "BMP9 is Produced by Hepatocytes and Circulates Mainly in an Active Mature Form Complexed to Its Prodomain", Cell. Mol. Life Sci. 69:313-324 (2012).
Burton V.J. et al., "Bone Morphogenetic Protein Receptor II Regulates Pulmonary Artery Endothelial Cell Barrier Function", Blood 117(1):333-341 (Jan. 6, 2011).
Burton V.J. et al., "Attenuation of Leukocyte Recruitment Via CXCR1/2 Inhibition Stops the Progression of PAH in Mice With Genetic Ablation of Endothelial BMPR-II", Blood 118(17):4750-4758 (Oct. 27, 2011).
Chen H. et al., "Context-Dependent Signaling Defines Roles of BMP9 and BMP10 in Embryonic and Postnatal Development", PNAS 110(29):11887-11892 (Jul. 16, 2013).
Chen H. et al., "Overexpression of Bone Morphogenetic Protein 10 in Myocardium Disrupts Cardiac Postnatal Hypertrophic Growth", The Journal of Biological Chemistry 281(37):27481-27497 (Sep. 15, 2006).

(Continued)

*Primary Examiner* — Elizabeth C. Kemmerer
(74) *Attorney, Agent, or Firm* — Scully, Scott, Murphy & Presser, P.C.

(57) ABSTRACT

The invention relates to a polypeptide selected from bone morphogenetic protein 10 (BMP10), or a bone morphogenetic protein 9 (BMP9) variant lacking osteogenic activity, for use in the treatment of a vascular disease or a respiratory disease. The invention also relates to novel BMP9 variants and to pharmaceutical compositions comprising said polypeptides.

8 Claims, 7 Drawing Sheets

Specification includes a Sequence Listing.

(56) References Cited

OTHER PUBLICATIONS

Chen H. et al., "BMP10 is Essential for Maintaining Cardiac Growth During Murine Cardiogenesis", Development 131(9):2219-2231 (2004).
David L. et al., "Bone Morphogenetic Protein-9 is a Circulating Vascular Quiescence Factor", Circulation Research 102:914-922 (Feb. 2008) and Supplemental Material.
David L. et al., "Identification of BMP9 and BMP10 as Functional Activators of the Orphan Activin Receptor-Like Kinase 1 (ALK1) in Endothelial Cells", Blood 109(5):1953-1961 (Mar. 1, 2007).
Deng Z. et al., "Familial Primary Pulmonary Hypertension (Gene PPH1) is Caused by Mutations in the Bone Morphogenetic Protein Receptor II Gene", Am. J. Hum. Genet. 67:737 744 (2000).
Evans J.D.W. et al., "BMPR2 Mutations and Survival in Pulmonary Arterial Hypertension: an Individual Participant Data Meta-Analysis", The Lancet 4:129-137 (Feb. 2016).
Fuchigami S. et al., "Recombinant Human Bone Morphogenetic Protein-9 Potently Induces Osteogenic Differentiation of Human Periodontal Ligament Fibroblasts", European Journal of Oral Sciences 124:151-157 (2016).
Gaine S.P. et al., "Primary Pulmonary Hypertension", The Lancet 352:719-725 (Aug. 29, 1998).
Harrison RE et al., "Molecular and Functional Analysis Identifies ALK-1 as the Predominant Cause of Pulmonary Hypertension Related to Hereditary Haemorrhagic Telangiectasia", J Med Genet 40:865-871 (2003).
Herrera B. et al., "A Rapid and Sensitive Bioassay for the Simultaneous Measurement of Multiple Bone Morphogenetic Proteins. Identification and Quantification of BMP4, BMP6 and BMP9 in Bovine and Human Serum", BMC Cell Biology vol. 10(20) (11 pages) (2009).
Hong K-H et al., "Genetic Ablation of the Bmpr2 Gene in Pulmonary Endothelium is Sufficient to Predispose to Pulmonary Arterial Hypertension", Circulation 118:722-730 (Aug. 12, 2008).
Jiang H. et al., "The Prodomain-Bound Form of Bone Morphogenetic Protein 10 is Biologically Active on Endothelial Cells", The Journal of Biological Chemistry 291(6):12954-2966 (Feb. 5, 2016).
Kang Q. et al., "Characterization of the Distinct Orthotopic Bone-Forming Activity of 14 BMPs Using Rcombinant Adenovirus-Mediated Gene Delivery", Gene Therapy 11:1312-1320 (2004).
Kienast Y. et al., "Rapid Activation of Bone Morphogenic Protein 9 by Receptor-Mediated Displacement of Pro-Domains", J. Biol. Chem. 291(7):13395-3410 (2016).
Kim CW et al., "Anti-Inflammatory and Antiatherogenic Role of BMP Receptor II in Endothelial Cells", Arterioscler Thromb Vase Biol 33:1350-1359 (Jun. 2013), and Supplemental Material.
Lane K.B. et al., "Heterozygous Germline Mutations in BMPR2, Encoding a TGF-B Receptor, Cause Familial Primary Pulmonary Hypertension", Nature Genetics 26:81-84 (Sep. 2000).
Laux D.W. et al., "Circulating Bmp10 Acts Through Endothelial Alk1 to Mediate Flow-Dependent Arterial Quiescence", Development 140(16):3403-3412 (Jun. 5, 2013) and Supplemental Material.
Long L. et al., "Selective Enhancement of Endothelial BMPR-II With BMP9 Reverses Pulmonary Arterial Hypertension", Nature Medicine 21(7):777-785 (Jul. 2015) and Supplemental Material.
Long L. et al., "Altered Bone Morphogenetic Protein and Transforming Growth Factor-B Signaling in Rat Models of Pulmonary Hypertension", Circulation 119:566-576 (2009) and Supplemental Material.
Luo J. et al., "TGFB/BMP Type I Receptors ALK1 and ALK2 are Essential for BMP9-Induced Osteogenic Siganling in Mesenchymal Stem Cells", The Journal of Biological Chemistry 285(38):29588-29598 (Sep. 17, 2010) and Supplemental Material.
Luther G. et al., "BMP-9 Induced Osteogenic Differentiation of Mesenchymal Stem Cells: Molecular Mechanism and Therapeutic Potential", Current Gene Therapy 11 (3):229-240 (2011).
Mi L-Z et al., "Structure of Bone Morphogenetic Protein 9 Procomplex", PNAS 112(12):3710-3715 (Mar. 24, 2015).

Miller A.F. et al., "Bone Morphogenetic Protein-9—An Autocrine/Paracrine Cytokine in the Liver", The Journal of Biological Chemistry 275(24):17937-17945 (Jun. 16, 2000).
Miyazono K. et al., "BMP Receptor Signaling: Transcriptional Targets, Regulation of Signals, and Signaling Cross-Talk", Cytokine & Growth Factor Reviews 16:251-263 (2005).
Morrell N.W. et al., "Cellular and Molecular Basis of Pulmonary Arterial Hypertension", Journal of the American College of Cardiology 54(1), Suppl S:S20-S31 (Jun. 30, 2009).
Euhaus H. et al., "Heart Specific Expression of Mouse BMP-10 a Novel Member of the TGF-B Superfamily", Mechanisms of Development 80:181-184 (1999).
Reynolds A.M. et al., "Bone Morphogenetic Protein Type 2 Receptor Gene Therapy Attenuates Hypoxic Pulmonary Hypertension", Am J Physiol Lung Cell Mol Physiol 292:L1182-L1192 (2007).
Reynolds A.M. et al., "Targeted Gene Delivery of BMPR2 Attenuates Pulmonary Hypertension", Eur Respir J 39(2):329-343 (2012).
Ricard N. et al., "BMP9 and BMP10 are Critical for Postnatal Retinal Vascular Remodeling", Blood 119(25):6162-6171 (Jun. 21, 2012).
Scharpfenecker M. et al., "BMP-9 Signals Via ALK1 and Inhibits BFGF-lnduced Endothelial Cell Proliferation and VEGF-Stimulated Angiogenesis", Journal of Cell Science 120(6):964-972 (2007).
Sengle G. et al., "Prodomains of Transforming Growth Factor B (TGFB) Superfamily Members Specify Different Functions", The Journal of Biological Chemistry 286(7):5087-5099 (Feb. 18, 2011).
Souza T.A. et al., "Proteomic Identification and Functional Validation of Activins and Bone Morphogenetic Protein 11 as Candidate Novel Muscle Mass Regulators", Molecular Endocrinology 22(12):2689-2702 (Dec. 2008).
Spiekerkoeter E. et al., "FK506 Activates BMPR2, Rescues Endothelial Dysfunction, and Reverses Pulmonary Hypertension", The Journal of Clinical Investigation 123(8):3600-3613 (Aug. 2013).
Taraseviciene-Stewart L. et al., "Inhibition of the VEGF Receptor 2 Combined With Chronic Hypoxia Causes Dell Death-Dependent Pulmonary Endothelial Cell Proliferation and Severe Pulmonary Hypertension", FASEB J. 15:427-438 (2001).
Teichert-Kuliszewska K. et al., "Bone Morphogenetic Protein Receptor-2 Signaling Promotes Pulmonary Arterial Endothelial Cell Survival", Circulation Research 98:209-217 (Feb. 3, 2006) and Supplemental Material.
Thomson Jr et al., "Sporadic Primary Pulmonary Hypertension is Associated With Germline Mutations of the Gene Encoding BMPR-II, a Receptor Member of the TGF-B Family", J Med Genet 37:741-745 (2000).
Townson S.A. et al., "Specificity and Structure of a High Affinity Activin Receptor-Like Kinase 1 (ALK1) Signaling Complex", The Journal of Biological Chemistry 287(33):27313-27325 (Aug. 10, 2012) and Supplemental Material.
Trembath R.C. et al., "Clinical and Molecular Genetic Features of Pulmonary Hypertension in Patients With Hereditary Hemorrhagic Telangiectasia", The New England Journal of Medicine 345(5):325-334 (Aug. 2, 2001).
Upton P.D. et al., "Bone Morphogenetic Protein (BMP) and Activin Type II Receptors Balance BMP9 Signals Medicated by Activin Receptor-Like Kinase-1 in Human Pulmonary Artery Endothelial Cells", The Journal of Biological Chemistry 284(23):15794-15804 (Jun. 5, 2009).
Upton P.D. et al., "Functional Characterization of Bone Morphogenetic Protein Binding Sites and Smad1/5 Activation in Human Vascular Cells", Molecular Pharmacology 73(2):539-552 (2008) and Supplemental Material.
Wilson D.W. et al., "Mechanisms and Pathology of Monocrotaline Pulmonary Toxicity", Critical Reviews in Toxicology 22(5/6):307-325 (1992).
Wu N. et al., "Identification and Analysis of Type II TGF-B Receptors in BMP-9-Induced Osteogenic Differentiation of C3H10T1/2 Mesenchymal Stem Cells", Acta Biochim Biophys Sin 42(10):699-708 (2010).
Yang J. et al., "Mutations in Bone Morphogenetic Protein Type II Receptor Cause Dysregulation of Id Gene Expression in Pulmonary Artery Smooth Muscle Cells", Circulation Research 102:1212-1221 (May 23, 2008) and Supplemental Material.

(56) References Cited

OTHER PUBLICATIONS

Yeager M.E. et al., "Microsatellite Instability of Endothelial Cell Growth and Apoptosis Genes Within Plexiform Lesions in Primary Pulmonary Hyptertension", Circulation Research 88:e2-e11 (Jan. 5-19, 2001).
Zhang W. et al., "Tbx20 Transcription Factor is a Downstream Mediator for Bone Morphogenetic Protein-10 in Regulating Cardiac Ventricular Wall Development and Function", The Journal of Biological Chemistry 286(42):36820-36829 (Oct. 21, 2011) and Supplemental Material.
International Search Report and Written Opinion dated Sep. 30, 2015 received in International Application No. PCT/GB2015/051989.
Jiloa-Aguirre A. et al., "Pharmacologic Rescue of Confomnationally-Defective Proteins: Implications for the Treatment of Human Disease", Traffic, (2004), 5:821-837.
Bernier V. et al., "Pharmacological chaperone action on G-protein-coupled receptors", Curr. Opin. Pharmacol., (2004), 4:528-533.
Tokuriki N. et al., "Stability effects of mutations and protein evolvability", Curr. Opin. Struc. Biol., (2009), 19:596-604.
Bhattacharya R. et al., "Impact of genetic variation on three dimensional structure and function of proteins", PLoS ONE, (2017), 12(3):e0171355, 1-22.
Helm G.A. et al., "Use of bone morphogenetic protein-9 gene therapy to induce spinal arthrodesis in the rodent", J. Neurosurg. (Spine 2), (2000), 92, pp. 191-196.
Belikov V.G. et al., "Pharmaceutical Chemistry in Two Parts", Pharmaceutical Chemistry, M., Higher School, pp. 43-47 (1993), together with English translation.
Jakubke H.D. et al., "Amino Acids, Peptides, and Proteins", Chemistry Editorial Board, M: Mir, pp. 92-94 (1985), together with English translation.
Kholodov L.E. et al. (1985) Klinicheskaya pharmakokinetika (Clinical Pharmacokinetics), Meditsina, pp. 83-98, 134-138, 160, 378-380, together with English translation.
Russian Office Action dated Feb. 28, 2019 in Russian Patent Application No. 2017102381/04(004166), together with English translation.
Russian Office Action dated Apr. 10, 2020 in Russian Patent Application No. 2017102381/14(004166), together with English translation.
Salmon, R.M. et al.,"Molecular basis of ALK1-mediated signalling by BMP9/BMP10 and their prodomain-bound forms", Nature Communications, pp. 1-16 (2020) https://doi.org/10.1038/s41467-020-15425-3.
Miahlawat, P. et al., "Structure of the Alk1 extracellular domain and characterization of its BMP binding properties", Biochemistry, 51(32): 6328-6341 (Aug. 14, 2012).
Cheng H. et al., "Osteogenic Activity of the Fourteen Types of Human Bone Morphogenetic Proteins (BMPs)", The Journal of Bone and Joint Surgery 85A(8):1545-1552 (Aug. 2003).
Kirsch T. et al., "BMP-2 Antagonists Emerge from Alterations in the Low-Affinity Binding Epitope for Receptor BMPR-II", The EMBO Journal 19(13):3314-3324 (2000).
Lamplot J D et al., "BMP9 Signaling in Stem Cell Differentiation and Osteogenesis", Am J Stem Cell 2(1):1-21 (2013).
Li JZ et al., "Osteogenic Potential of Five Different Recombinant Human Bone Morphogenetic Protein Adenoviral Vectors in the Rat", Gene Therapy 10:1735-1743 (2003).
Nicolls M.R. et al., "New Models of Pulmonary Hypertension Based on VEGF Receptor Blockade-Induced Endothelial Cell Apoptosis", Pulmonary Circulation 2(4):434-442 (Oct.-Dec. 2012).
Southwood M. et al., "Regulation of Bone Morphogenetic Protein Signalling in Human Pulmonary Vascular Development", Journal of Pathology 214:85-95 (2008).
Vitali S.H. et al., "The Sugen 5416/Hypoxia Mouse Model of Pulmonary Hypertension Revisited: Long-Term Follow-Up", Pulmonary Circulation 4(4):619-629 (Dec. 2014).
Response to Opposition and Supporting Data, filed on Apr. 23, 2021 in European Patent No. 3166628 B1.
Morrell, N.M. et al., "Anticipated classes of new medications and molecular targets for pulmonary arterial hypertension", Pulmonary Circulation, vol. 3, No. 1, pp. 226-244 (Jan.-Mar. 2013).
European Patent Office Communication of a Notice of Opposition dated Oct. 6, 2020 in corresponding European Patent Application No. 15739658.1.
Zhang, Y. et al., "Cell Therapy Using Articular Chondrocytes Overexpressing BMP-7 or BMP-10 in a Rabbit Disc Organ Culture Model", Spine, vol. 33. No. 8, pp. 831-838 (2008).
Gräf et al., "Identification of Rare Sequence Variation Underlying Heritable Pulmonary Arterial Hypertension", Mature Communications 9(1416):1-16 (2018).
Jiang Q. et al., "Dysregulation of BMP9/BMPR2/SMAD Signalling Pathway Contributes to Pulmonary Fibrosis and Pulmonary Hypertension Induced by Bleomycin in Rats", The British Pharmacological Society 178:203-216 (2021).
Nang X-J et al., "Germline BMP9 Mutation Causes Idiopathic Pulmonary Arterial Hypertension", Eur Respir J 53:1801609 (2019).
Abe K. et al., "Formation of Plexiform Lesions in Experimental Severe Pulmonary Arterial Hypertension", Circulation 121:2747-2754 (Jun. 29, 2010).
Ciuclan L. et al., "A Novel Murine Model of Severe Pulmonary Arterial Hypertension", American Journal of Respiratory and Critical Medicine 184:1171-1182 (2011).
Hassanisaber H. et al., "Effect of BMP-9 on Endothelial Cells and its Role in Atherosclerosis", Frontiers in Bioscience Landmark 24:994-1023 (Mar. 1, 2019).
Freitas G.P. et al., "Mesenchymal Stem Cells Overexpressing BMP-9 by CRISPR-Cas9 Present High In Vitro Dsteogenic Potential and Enhance In Vivo Bone Formation", Gene Therapy 28(12):748-759 (Dec. 2021).
Leblanc E. et al., "BMP-9-Induced Muscle Heterotopic Ossification Requires Changes to the Skeleton Muscle Microenvironment", Journal of Bone and Mineral Research 26(6):1166-1177 (Jun. 2011).
Second Declaration of Jinquan Luo in EPO Opposition against EP 3 166 628 B1 (Mar. 28, 2022).
Declaration of Jinquan Luo in EPO Opposition against EP 3 166 628 B1 (Sep. 7, 2021).
EPO Communication dated Jul. 13, 2022 regarding the result of Opposition of EP 3 166 628 B1 (Jul. 13, 2022).
Patentee's Response To Summons in European Patent No. 3166628 B1 (May 13, 2022).
Letter from Opponent in European Patent No. 3166628 (Mar. 30, 2022).
EPO Summons to Attend Oral Proceedings with Preliminary Opinion dated Dec. 10, 2021 received in EP 3 166 628 B1.
Letter Regarding Observations on Behalf of the Patentee in European Patent No. 3166628 B1 (Nov. 12, 2021).
Letter Regarding Opponent's Comments and Observations on the Patentee's Response in European Patent No. 3166628 (Sep. 8, 2021).

\* cited by examiner

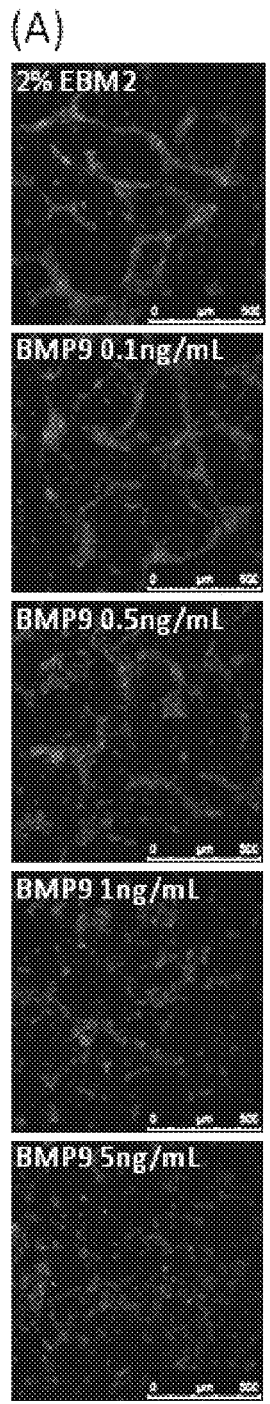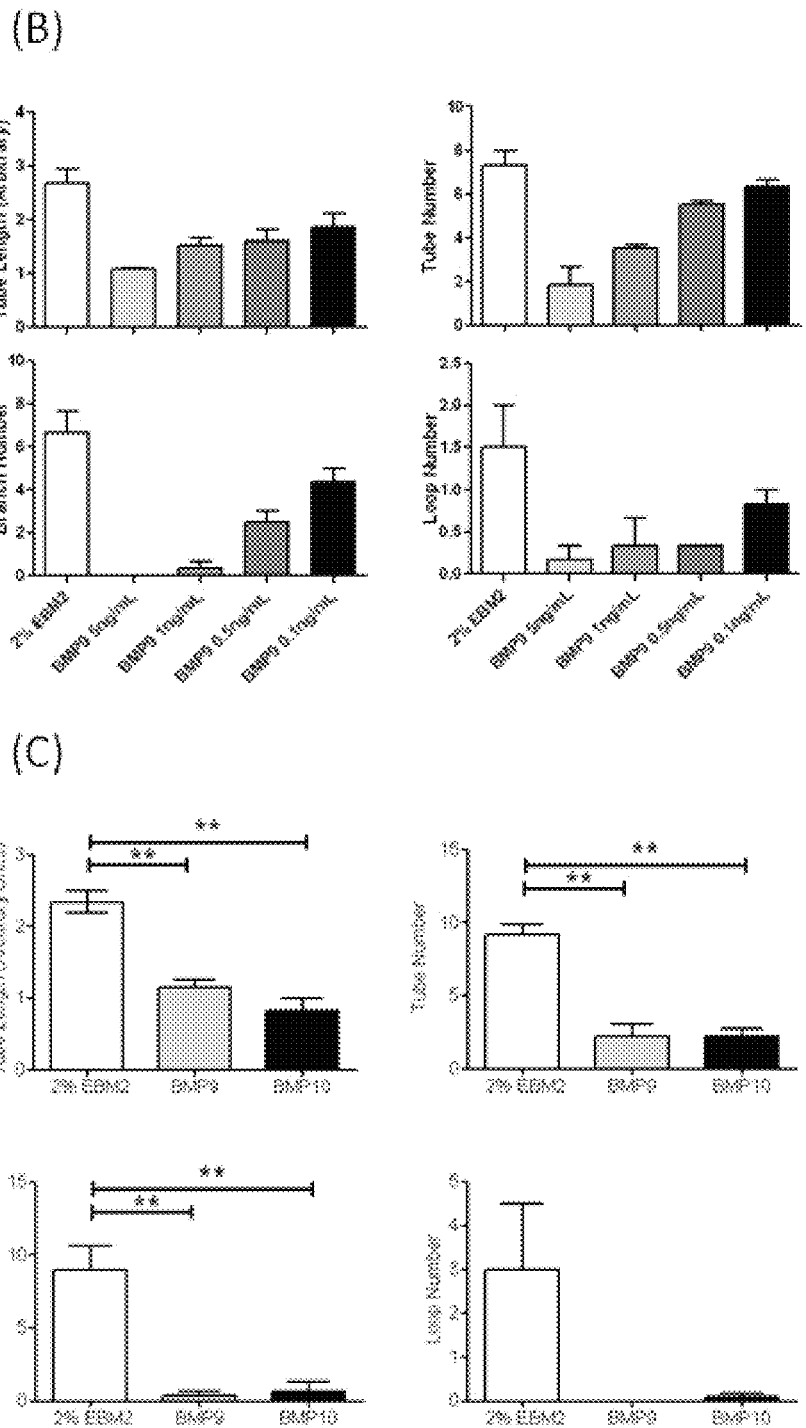
FIG. 8A - 8C

SEQUENCE LISTING

```
<160> NUMBER OF SEQ ID NOS: 6

<210> SEQ ID NO 1
<211> LENGTH: 1275
<212> TYPE: DNA
<213> ORGANISM: Human

<400> SEQUENCE: 1
atgggctctc tggtcctgac actgtgcgct cttttctgcc tggcagctta cttggtttct      60
ggcagcccca tcatgaacct agagcagtct cctctgaag aagatatgtc cctctttggt     120
gatgttttct cagagcaaga cggtgtcgac tttaacacac tgctccagag catgaaggat     180
gagtttctta agacactaaa cctctctgac atccccacgc aggattcagc caaggtggac     240
ccaccagagt acatgttgga actctacaac aaatttgcaa cagatcggac ctccatgccc     300
tctgccaaca tcattaggag tttcaagaat gaagatctgt tttcccagcc ggtcagtttt     360
aatgggctcc gaaaataccc cctcctcttc aatgtgtcca ttcctcacca tgaagaggtc     420
atcatggctg aacttaggct atacacactg gtgcaaaggg atcgtatgat atacgatgga     480
gtagaccgga aaattaccat ttttgaagtg ctggagagca aagggataa tgagggagaa     540 agaaacatgc tggtcttggt gtctggggag atatatggaa ccaacagtga gtgggagact     600
tttgatgtca cagatgccat cagacgttgg caaaagtcag gctcatccac ccaccagctg     660
```

-continued

```
gaggtccaca ttgagagcaa acacgatgaa gctgaggatg ccagcagtgg acggctagaa      720
atagatacca gtgcccagaa taagcataac cctttgctca tcgtgttttc tgatgaccaa      780
agcagtgaca aggagaggaa ggaggaactg aatgaaatga tttcccatga gcaacttcca      840
gagctggaca acttgggcct ggatagcttt tccagtggac ctggggaaga ggctttgttg      900
cagatgagat caaacatcat ctatgactcc actgcccgaa tcagaaggaa cgccaaagga      960
aactactgta agaggacccc gctctacatc gacttcaagg agattgggtg ggactcctgg     1020
atcatcgctc cgcctggata cgaagcctat gaatgccgtg gtgtttgtaa ctaccccctg     1080
gcagagcatc tcacacccac aaagcatgca attatccagg ccttggtcca cctcaagaat     1140
tcccagaaag cttccaaagc tgctgtgtg cccacaaagc tagagcccat ctccatcctc     1200
tatttagaca aggcgtcgt cacctacaag tttaaatacg aaggcatggc cgtctccgaa     1260
tgtggctgta gatag                                                      1275
```

<210> SEQ ID NO 2
<211> LENGTH: 424
<212> TYPE: PRT
<213> ORGANISM: Human

<400> SEQUENCE: 2

```
Met Gly Ser Leu Val Leu Thr Leu Cys Ala Leu Phe Cys Leu Ala Ala
1               5                   10                  15

Tyr Leu Val Ser Gly Ser Pro Ile Met Asn Leu Glu Gln Ser Pro Leu
            20                  25                  30

Glu Glu Asp Met Ser Leu Phe Gly Asp Val Phe Ser Glu Gln Asp Gly
        35                  40                  45

Val Asp Phe Asn Thr Leu Leu Gln Ser Met Lys Asp Glu Phe Leu Lys
    50                  55                  60

Thr Leu Asn Leu Ser Asp Ile Pro Thr Gln Asp Ser Ala Lys Val Asp
65                  70                  75                  80

Pro Pro Glu Tyr Met Leu Glu Leu Tyr Asn Lys Phe Ala Thr Asp Arg
                85                  90                  95

Thr Ser Met Pro Ser Ala Asn Ile Ile Arg Ser Phe Lys Asn Glu Asp
            100                 105                 110

Leu Phe Ser Gln Pro Val Ser Phe Asn Gly Leu Arg Lys Tyr Pro Leu
        115                 120                 125

Leu Phe Asn Val Ser Ile Pro His His Glu Glu Val Ile Met Ala Glu
    130                 135                 140

Leu Arg Leu Tyr Thr Leu Val Gln Arg Asp Arg Met Ile Tyr Asp Gly
145                 150                 155                 160

Val Asp Arg Lys Ile Thr Ile Phe Glu Val Leu Glu Ser Lys Gly Asp
                165                 170                 175

Asn Glu Gly Glu Arg Asn Met Leu Val Leu Val Ser Gly Glu Ile Tyr
            180                 185                 190

Gly Thr Asn Ser Glu Trp Glu Thr Phe Asp Val Thr Asp Ala Ile Arg
        195                 200                 205

Arg Trp Gln Lys Ser Gly Ser Ser Thr His Gln Leu Glu Val His Ile
    210                 215                 220

Glu Ser Lys His Asp Glu Ala Glu Asp Ala Ser Ser Gly Arg Leu Glu
225                 230                 235                 240

Ile Asp Thr Ser Ala Gln Asn Lys His Asn Pro Leu Leu Ile Val Phe
                245                 250                 255

Ser Asp Asp Gln Ser Ser Asp Lys Glu Arg Lys Glu Glu Leu Asn Glu
```

```
                260                 265                 270
Met Ile Ser His Glu Gln Leu Pro Glu Leu Asp Asn Leu Gly Leu Asp
            275                 280                 285

Ser Phe Ser Ser Gly Pro Gly Glu Glu Ala Leu Leu Gln Met Arg Ser
        290                 295                 300

Asn Ile Ile Tyr Asp Ser Thr Ala Arg Ile Arg Arg Asn Ala Lys Gly
305                 310                 315                 320

Asn Tyr Cys Lys Arg Thr Pro Leu Tyr Ile Asp Phe Lys Glu Ile Gly
                325                 330                 335

Trp Asp Ser Trp Ile Ile Ala Pro Pro Gly Tyr Glu Ala Tyr Glu Cys
                340                 345                 350

Arg Gly Val Cys Asn Tyr Pro Leu Ala Glu His Leu Thr Pro Thr Lys
            355                 360                 365

His Ala Ile Ile Gln Ala Leu Val His Leu Lys Asn Ser Gln Lys Ala
        370                 375                 380

Ser Lys Ala Cys Cys Val Pro Thr Lys Leu Glu Pro Ile Ser Ile Leu
385                 390                 395                 400

Tyr Leu Asp Lys Gly Val Val Thr Tyr Lys Phe Lys Tyr Glu Gly Met
                405                 410                 415

Ala Val Ser Glu Cys Gly Cys Arg
            420

<210> SEQ ID NO 3
<211> LENGTH: 1290
<212> TYPE: DNA
<213> ORGANISM: Human

<400> SEQUENCE: 3
atgtgtcctg gggcactgtg ggtggccctg cccctgctgt ccctgctggc tggctcccta      60 cagggaagc cactgcagag ctggggacga gggtctgctg ggggaaacgc ccacagccca     120 ctggggggtgc ctggaggtgg gctgcctgag cacaccttca acctgaagat gtttctggag     180
aacgtgaagg tggatttcct gcgcagcctt aacctgagtg gggtcccttc gcaggacaaa     240
accagggtgg agccgccgca gtacatgatt gacctgtaca caggtacac gtccgataag      300 tcgactacgc cagcgtccaa cattgtgcgg agcttcagca tggaagatgc catctcccata    360 actgccacag aggacttccc cttccagaag cacatcttgc tcttcaacat ctccattcct     420
aggcatgagc agatcaccag agctgagctc cgactctatg tctcctgtca aaatcacgtg     480
gacccctctc atgacctgaa aggaagcgtg gtcatttatg atgttctgga tggaacagat     540
gcctgggata gtgctacaga gaccaagacc ttcctggtgt cccaggacat tcaggatgag     600
ggctgggaga ccttggaagt gtccagcgcc gtgaagcgct gggtccggtc cgactccacc     660
aagagcaaaa ataagctgga agtgactgtg agagccaca ggaagggctg cgacacgctg      720
gacatcagtg tcccccagg ttccagaaac ctgccccttct tgttgtcttc tccaatgac     780 cacagcagtg ggaccaagga gaccaggctg agctgaggg agatgatcag ccatgaacaa     840
gagagcgtgc tcaagaagct gtccaaggac ggctccacag aggcaggtga gcagtcac      900 gaggaggaca cggatggcca cgtggctgcg ggtcgactt tagccaggcg gaaaaggagc      960 gccgggctg cagccactg tcaaaagacc tccctgcggg taaacttcga ggacatcggc     1020
tgggacagct ggatcattgc acccaaggag tatgaagcct acgagtgtaa gggcggctgc    1080 ttcttccccct ggctgacga tgtgacgccg acgaaacacg ctatcgtgca gaccctggtg    1140
catctcaagt tccccacaaa ggtgggcaag gcctgctgtg tgcccaccaa actgagcccc    1200
```

```
atctccgtcc tctacaagga tgacatgggg gtgcccaccc tcaagtacca ttacgagggc    1260
atgagcgtgg cagagtgtgg gtgcaggtag                                     1290
```

<210> SEQ ID NO 4
<211> LENGTH: 429
<212> TYPE: PRT
<213> ORGANISM: Human

<400> SEQUENCE: 4

| | | | | | | | | | | | | | | |
|---|---|---|---|---|---|---|---|---|---|---|---|---|---|---|
| Met | Cys | Pro | Gly | Ala | Leu | Trp | Val | Ala | Leu | Pro | Leu | Leu | Ser | Leu |
| 1 | | | | 5 | | | | | 10 | | | | | 15 |
| Leu | Ala | Gly | Ser | Leu | Gln | Gly | Lys | Pro | Leu | Gln | Ser | Trp | Gly | Arg |
| | | | | 20 | | | | | 25 | | | | | 30 |

Met Cys Pro Gly Ala Leu Trp Val Ala Leu Pro Leu Leu Ser Leu
1               5                   10                  15

Ala Gly Ser Leu Gln Gly Lys Pro Leu Gln Ser Trp Gly Arg Ser
            20                  25                  30

Ala Gly Gly Asn Ala His Ser Pro Leu Gly Val Pro Gly Gly Leu
            35                  40              45

Pro Glu His Thr Phe Asn Leu Lys Met Phe Leu Glu Asn Val Lys Val
        50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
                85                  90                  95

Thr Ser Asp Lys Ser Thr Thr Pro Ala Ser Asn Ile Val Arg Ser Phe
                100                 105                 110

Ser Met Glu Asp Ala Ile Ser Ile Thr Ala Thr Glu Asp Phe Pro Phe
            115                 120                 125

Gln Lys His Ile Leu Leu Phe Asn Ile Ser Ile Pro Arg His Glu Gln
            130                 135                 140

Ile Thr Arg Ala Glu Leu Arg Leu Tyr Val Ser Cys Gln Asn His Val
145                 150                 155                 160

Asp Pro Ser His Asp Leu Lys Gly Ser Val Val Ile Tyr Asp Val Leu
                165                 170                 175

Asp Gly Thr Asp Ala Trp Asp Ser Ala Thr Glu Thr Lys Thr Phe Leu
            180                 185                 190

Val Ser Gln Asp Ile Gln Asp Glu Gly Trp Glu Thr Leu Glu Val Ser
            195                 200                 205

Ser Ala Val Lys Arg Trp Val Arg Ser Asp Ser Thr Lys Ser Lys Asn
            210                 215                 220

Lys Leu Glu Val Thr Val Glu Ser His Arg Lys Gly Cys Asp Thr Leu
225                 230                 235                 240

Asp Ile Ser Val Pro Pro Gly Ser Arg Asn Leu Pro Phe Phe Val Val
                245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
            275                 280                 285

Lys Asp Gly Ser Thr Glu Ala Gly Glu Ser Ser His Glu Glu Asp Thr
            290                 295                 300

Asp Gly His Val Ala Ala Gly Ser Thr Leu Ala Arg Arg Lys Arg Ser
305                 310                 315                 320

Ala Gly Ala Gly Ser His Cys Gln Lys Thr Ser Leu Arg Val Asn Phe
                325                 330                 335

Glu Asp Ile Gly Trp Asp Ser Trp Ile Ile Ala Pro Lys Glu Tyr Glu
            340                 345                 350

-continued

```
Ala Tyr Glu Cys Lys Gly Gly Cys Phe Pro Leu Ala Asp Asp Val
            355                 360                 365

Thr Pro Thr Lys His Ala Ile Val Gln Thr Leu Val His Leu Lys Phe
370                 375                 380

Pro Thr Lys Val Gly Lys Ala Cys Cys Val Pro Thr Lys Leu Ser Pro
385                 390                 395                 400

Ile Ser Val Leu Tyr Lys Asp Asp Met Gly Val Pro Thr Leu Lys Tyr
                405                 410                 415

His Tyr Glu Gly Met Ser Val Ala Glu Cys Gly Cys Arg
            420                 425

<210> SEQ ID NO 5
<211> LENGTH: 429
<212> TYPE: PRT
<213> ORGANISM: Artificial
<220> FEATURE:
<223> OTHER INFORMATION: D366A BMP9 Variant

<400> SEQUENCE: 5

Met Cys Pro Gly Ala Leu Trp Val Ala Leu Pro Leu Leu Ser Leu Leu
1               5                   10                  15

Ala Gly Ser Leu Gln Gly Lys Pro Leu Gln Ser Trp Gly Arg Gly Ser
            20                  25                  30

Ala Gly Gly Asn Ala His Ser Pro Leu Gly Val Pro Gly Gly Gly Leu
        35                  40                  45

Pro Glu His Thr Phe Asn Leu Lys Met Phe Leu Glu Asn Val Lys Val
    50                  55                  60

Asp Phe Leu Arg Ser Leu Asn Leu Ser Gly Val Pro Ser Gln Asp Lys
65                  70                  75                  80

Thr Arg Val Glu Pro Pro Gln Tyr Met Ile Asp Leu Tyr Asn Arg Tyr
                85                  90                  95

Thr Ser Asp Lys Ser Thr Thr Pro Ala Ser Asn Ile Val Arg Ser Phe
            100                 105                 110

Ser Met Glu Asp Ala Ile Ser Ile Thr Ala Thr Glu Asp Phe Pro Phe
        115                 120                 125

Gln Lys His Ile Leu Leu Phe Asn Ile Ser Ile Pro Arg His Glu Gln
    130                 135                 140

Ile Thr Arg Ala Glu Leu Arg Leu Tyr Val Ser Cys Gln Asn His Val
145                 150                 155                 160

Asp Pro Ser His Asp Leu Lys Gly Ser Val Val Ile Tyr Asp Val Leu
                165                 170                 175

Asp Gly Thr Asp Ala Trp Asp Ser Ala Thr Glu Thr Lys Thr Phe Leu
            180                 185                 190

Val Ser Gln Asp Ile Gln Asp Glu Gly Trp Glu Thr Leu Glu Val Ser
        195                 200                 205

Ser Ala Val Lys Arg Trp Val Arg Ser Asp Ser Thr Lys Ser Lys Asn
    210                 215                 220

Lys Leu Glu Val Thr Val Glu Ser His Arg Lys Gly Cys Asp Thr Leu
225                 230                 235                 240

Asp Ile Ser Val Pro Pro Gly Ser Arg Asn Leu Pro Phe Phe Val Val
                245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
        275                 280                 285
```

```
Lys Asp Gly Ser Thr Glu Ala Gly Glu Ser Ser His Glu Glu Asp Thr
290                 295                 300
Asp Gly His Val Ala Ala Gly Ser Thr Leu Ala Arg Arg Lys Arg Ser
305                 310                 315                 320
Ala Gly Ala Gly Ser His Cys Gln Lys Thr Ser Leu Arg Val Asn Phe
            325                 330                 335
Glu Asp Ile Gly Trp Asp Ser Trp Ile Ile Ala Pro Lys Glu Tyr Glu
            340                 345                 350
Ala Tyr Glu Cys Lys Gly Cys Phe Phe Pro Leu Ala Ala Asp Val
        355                 360                 365
Thr Pro Thr Lys His Ala Ile Val Gln Thr Leu Val His Leu Lys Phe
370                 375                 380
Pro Thr Lys Val Gly Lys Ala Cys Cys Val Pro Thr Lys Leu Ser Pro
385                 390                 395                 400
Ile Ser Val Leu Tyr Lys Asp Asp Met Gly Val Pro Thr Leu Lys Tyr
                405                 410                 415
His Tyr Glu Gly Met Ser Val Ala Glu Cys Gly Cys Arg
            420                 425
```

<210> SEQ ID NO 6
<211> LENGTH: 429
<212> TYPE: PRT
<213> ORGANISM: Artificial
<220> FEATURE:
<223> OTHER INFORMATION: D408A BMP9 Variant

<400> SEQUENCE: 6

```
Met Cys Pro Gly Ala Leu Trp Val Ala Leu Pro Leu Leu Ser Leu Leu
1               5                   10                  15
Ala Gly Ser Leu Gln Gly Lys Pro Leu Gln Ser Trp Gly Arg Gly Ser
            20                  25                  30
Ala Gly Gly Asn Ala His Ser Pro Leu Gly Val Pro Gly Gly Gly Leu
        35                  40                  45
Pro Glu His Thr Phe Asn Leu Lys Met Phe Leu Glu Asn Val Lys Val
50                  55                  60
Asp Phe Leu Arg Ser Leu Asn Leu Ser Gly Val Pro Ser Gln Asp Lys
65                  70                  75                  80
Thr Arg Val Glu Pro Pro Gln Tyr Met Ile Asp Leu Tyr Asn Arg Tyr
                85                  90                  95
Thr Ser Asp Lys Ser Thr Thr Pro Ala Ser Asn Ile Val Arg Ser Phe
            100                 105                 110
Ser Met Glu Asp Ala Ile Ser Ile Thr Ala Thr Glu Asp Phe Pro Phe
        115                 120                 125
Gln Lys His Ile Leu Leu Phe Asn Ile Ser Ile Pro Arg His Glu Gln
130                 135                 140
Ile Thr Arg Ala Glu Leu Arg Leu Tyr Val Ser Cys Gln Asn His Val
145                 150                 155                 160
Asp Pro Ser His Asp Leu Lys Gly Ser Val Val Ile Tyr Asp Val Leu
                165                 170                 175
Asp Gly Thr Asp Ala Trp Asp Ser Ala Thr Glu Thr Lys Thr Phe Leu
            180                 185                 190
Val Ser Gln Asp Ile Gln Asp Glu Gly Trp Glu Thr Leu Glu Val Ser
        195                 200                 205
Ser Ala Val Lys Arg Trp Val Arg Ser Asp Ser Thr Lys Ser Lys Asn
210                 215                 220
```

```
Lys Leu Glu Val Thr Val Glu Ser His Arg Lys Gly Cys Asp Thr Leu
225                 230                 235                 240

Asp Ile Ser Val Pro Pro Gly Ser Arg Asn Leu Pro Phe Phe Val Val
                245                 250                 255

Phe Ser Asn Asp His Ser Ser Gly Thr Lys Glu Thr Arg Leu Glu Leu
            260                 265                 270

Arg Glu Met Ile Ser His Glu Gln Glu Ser Val Leu Lys Lys Leu Ser
        275                 280                 285

Lys Asp Gly Ser Thr Glu Ala Gly Glu Ser Ser His Glu Glu Asp Thr
    290                 295                 300

Asp Gly His Val Ala Ala Gly Ser Thr Leu Ala Arg Arg Lys Arg Ser
305                 310                 315                 320

Ala Gly Ala Gly Ser His Cys Gln Lys Thr Ser Leu Arg Val Asn Phe
                325                 330                 335

Glu Asp Ile Gly Trp Asp Ser Trp Ile Ile Ala Pro Lys Glu Tyr Glu
            340                 345                 350

Ala Tyr Glu Cys Lys Gly Gly Cys Phe Phe Pro Leu Ala Asp Asp Val
        355                 360                 365

Thr Pro Thr Lys His Ala Ile Val Gln Thr Leu Val His Leu Lys Phe
    370                 375                 380

Pro Thr Lys Val Gly Lys Ala Cys Cys Val Pro Thr Lys Leu Ser Pro
385                 390                 395                 400

Ile Ser Val Leu Tyr Lys Asp Ala Met Gly Val Pro Thr Leu Lys Tyr
                405                 410                 415

His Tyr Glu Gly Met Ser Val Ala Glu Cys Gly Cys Arg
            420                 425
```

THERAPEUTIC USE OF BONE MORPHOGENETIC PROTEINS

FIELD OF THE INVENTION

The invention relates to a polypeptide selected from bone morphogenetic protein 10 (BMP10), or a bone morphogenetic protein 9 (BMP9) variant lacking osteogenic activity, for use in the treatment of a vascular disease or a respiratory disease. The invention also relates to novel BMP9 variants and to pharmaceutical compositions comprising said polypeptides.

BACKGROUND OF THE INVENTION

Vascular disease is a pathological state of large and medium sized muscular arteries and is triggered by endothelial cell dysfunction. Because of factors like pathogens, oxidized LDL particles and other inflammatory stimuli, endothelial cells become activated. This leads to changes in their characteristics: endothelial cells start to excrete cytokines and chemokines and express adhesion molecules on their surface. This in turn results in recruitment of white blood cells (monocytes and lymphocytes), which can infiltrate the blood vessel wall. Stimulation of the smooth muscle cell layer with cytokines produced by endothelial cells and recruited white blood cells causes smooth muscle cells to proliferate and migrate towards the blood vessel lumen. This process causes thickening of the vessel wall, forming a plaque consisting of proliferating smooth muscle cells, macrophages and various types of lymphocytes. This plaque results in obstructed blood flow leading to diminished amounts of oxygen and nutrients, that reach the target organ. In the final stages, the plaque may also rupture causing the formation of clots, and as a result, strokes.

Respiratory disease is a medical term that encompasses pathological conditions affecting the organs and tissues that make gas exchange possible in higher organisms, and includes conditions of the upper respiratory tract, trachea, bronchi, bronchioles, alveoli, pleura and pleural cavity, and the nerves and muscles of breathing. Respiratory diseases range from mild and self-limiting, such as the common cold, to life-threatening entities like bacterial pneumonia, pulmonary embolism, and lung cancer.

Pulmonary arterial hypertension (PAH) is a rare vascular disease for which there is currently no cure. Heritable and idiopathic pulmonary arterial hypertension (PAH) are characterized by narrowing and obliteration of precapillary pulmonary arteries, secondary to proliferation and apoptosis resistance of smooth muscle cells, fibroblasts and endothelial cells (Morrell et al (2009) J Am Coll Cardiol 54. S20-31). The resulting increase in pulmonary vascular resistance causes severe elevation of pulmonary artery pressure, leading to right ventricular hypertrophy and ultimately death from right heart failure (Gaine and Rubin (1998) Lancet 352, 719-725).

The identification of heterozygous germline mutations in the gene encoding the bone morphogenetic protein type II receptor (BMPR-II) in 2000 (Lane et al Nat Genet 26, 81-84 (2000); Deng et al (2000) Am J Hum Genet 67, 737-744) provided major insight into the pathobiology of heritable PAH. Subsequent studies have also identified BMPR-II mutations in 15-40% of cases of idiopathic PAH (Thomson et al (2000) J Med Genet 37, 741-745), as well as reduced expression of BMPR-II as a feature of non-genetic forms of PAH in humans (Atkinson et al (2002) Circulation 105, 1672-1678) and animal models (Long et al (2009) Circulation 119, 566-576).

Genetic evidence also strongly implicates the endothelial cell as the key initiating cell type in PAH. Previous studies have shown that conditional deletion of BMPR-II in the endothelium is sufficient to induce PAH in a proportion of mice (Hong et al (2008) Circulation 118, 722-730) and that rescue of endothelial BMPR-II signaling in rodent models prevents or reverses experimental pulmonary hypertension (Reynolds et al (2012) Eur Respir J 39, 329-343; Reynolds et al (2007) Am J Physiol Lung Cell Mol Physiol 292, L1182-1192; Spiekerkoetter et al (2013) J Clin Invest 123, 3600-3613). More recently, it has been shown that selective enhancement of endothelial BMPR-II with BMP9 reverses pulmonary arterial hypertension (Long et al (2015) Nature Medicine 21, 777-785). In addition, mutations have now been reported in the type I receptor, ALK-1 (Trembath et al (2001) N Engl J Med 345, 325-334), and the type III receptor accessory protein, endoglin (Harrison et al (2003) J Med Genet 40, 865-871), in patients with PAH, both of which are almost exclusively expressed on the endothelium. Despite this evidence, the precise nature of the endothelial dysfunction in the pathobiology of PAH and the involvement of BMP signaling in this process remain points of contention. Although established PAH is characterized by the excessive clonal proliferation of pulmonary endothelial cells (Yeager et al (2001) Circ Res 88, E2-E11) as a component of obstructive cellular lesions, the initiation of disease pathology in both humans (Teichert-Kuliszewska et al (2006) Circ Res 98, 209-217) and animal models of disease (Wilson et al (1992) Crit Rev Toxicol 22, 307-325; Taraseviciene-Stewart et al (2001) Faseb J 15, 427-438) has been linked to a paradoxical increase in endothelial cell apoptosis. Additional studies have identified a role for endothelial BMPR-II loss in the exacerbation of vascular permeability and the altered translocation of leukocytes across the vascular wall (Burton et al (2011) Blood 117, 333-341; Burton et al (2011) Blood 118, 4750-4758; Kim et al (2013) Arterioscler Thromb Vasc Biol 33, 1350-1359).

While in vitro studies using pulmonary artery smooth muscle cells (PASMCs) have demonstrated that increasing concentrations of BMP ligand can overcome the loss of function associated with mutations in the BMP signaling pathway (Yang et al (2008) Circ Res 102, 1212-1221), to date, no study has therapeutically delivered BMP ligand in vivo to provide proof-of-concept for such an approach in the treatment of PAH. The complexity of the BMP signaling family, which is comprised of four type-II receptors, five type-I receptors and over twenty BMP ligands (Miyazono et al (2005) Cytokine Growth Factor Rev 16, 251-263), may account for the absence of such studies. Identifying an appropriate ligand to selectively target the pulmonary endothelium presents a significant challenge. Recently, BMPR-II was found to form a signaling complex with ALK-1 and signal specifically in response to BMP9 and 10 in microvascular endothelial cells (David et al (2007) Blood 109, 1953-1961).

WO 2005/113590 describes the use of BMP10 antagonists for the treatment of heart disorders. WO 2013/152213 describes the use of BMP9 and/or BMP 10 polypeptides for increasing red blood cell and/or hemoglobin levels in vertebrates. WO 2006/130022 describes an agonist or antagonist of BMPRII which is useful in the modulation of folliculogenesis and ovulation rate in female mammals. WO 2010/114833 describes pharmaceutical compositions for treating heart disease that include a bone morphogenetic protein. WO 94/26893 describes BMP-10 proteins, processes for producing them and their use in the treatment of bone and cartilage defects and in wound healing and related tissue repair. WO 95/24474 and WO 96/39431 describe the human BMP-10 polypeptide and DNA (RNA) encoding such polypeptide which are claimed to be useful in inducing de novo bone formation. WO 93/00432 and WO 95/33830 describe BMP-9 proteins, processes for producing them and their use in the treatment of bone and cartilage defects, wound healing and related tissue repair and in hepatic growth and function. WO 2010/115874 describes methods for treating pulmonary arterial hypertension by administering apelin/APJ targeting drugs. WO 2009/114180 and WO 2014/160203 describe small molecule inhibitors of BMP signaling which are claimed to be useful in the modulation of cell growth, differentiation, proliferation, and apoptosis, and thus may be useful for treating diseases or conditions associated with BMP signaling, including inflammation, cardiovascular disease, hematological disease, cancer, and bone disorders, as well as for modulating cellular differentiation and/or proliferation. The small molecule inhibitors are also claimed to be useful in reducing circulating levels of ApoB-100 or LDL and treating or preventing acquired or congenital hypercholesterolemia or hyperlipoproteinemia; diseases, disorders, or syndromes associated with defects in lipid absorption or metabolism; or diseases, disorders, or syndromes caused by hyperlipidemia.

There is therefore a need to provide an effective treatment for vascular and respiratory diseases, in particular pulmonary arterial hypertension (PAH).

SUMMARY OF THE INVENTION

According to a first aspect of the invention, there is provided a polypeptide selected from bone morphogenetic protein 10 (BMP10), or a bone morphogenetic protein 9 (BMP9) variant lacking osteogenic activity, for use in the treatment of a vascular disease or a respiratory disease.

According to a further aspect of the invention, there is provided a method of treating a vascular disease or a respiratory disease which comprises administering to a subject in need thereof a therapeutically effective amount of a polypeptide selected from bone morphogenetic protein 10 (BMP10), or a bone morphogenetic protein 9 (BMP9) variant lacking osteogenic activity.

According to a further aspect of the invention, there is provided a pharmaceutical composition comprising BMP10, or a BMP9 variant lacking osteogenic activity, for use in the treatment of a vascular disease or a respiratory disease.

According to a further aspect of the invention, there is provided a BMP9 variant having the amino acid sequence of SEQ ID NO: 5.

According to a further aspect of the invention, there is provided a BMP9 variant having the amino acid sequence of SEQ ID NO: 6.

According to a further aspect of the invention, there is provided a pharmaceutical composition comprising the BMP9 variants as defined herein.

BRIEF DESCRIPTION OF THE FIGURES

FIGS. 8A-8C. BMP9 and BMP10 inhibit blood outgrowth endothelial cell (BOEC) tube formation in a collagen:fibronectin matrix. (A) Representative images of BOEC tubes in collagen gels stained with DAPI and FITC-ULEX. Networks form when in media alone (2% BBM2=EBM2 containing 2% FBS). Addition of increasing concentrations of BMP9 inhibits BOEC network formation, (B) Quantification of BOEC network parameters determined for 3 separate experiments demonstrating that BMP9 inhibits tube length and number, branching and loop formation in a concentration-dependent manner. (C) BMP9 and BMP10 that both ligands inhibit BOEC tube formation.

DETAILED DESCRIPTION OF THE INVENTION

Figure 1:
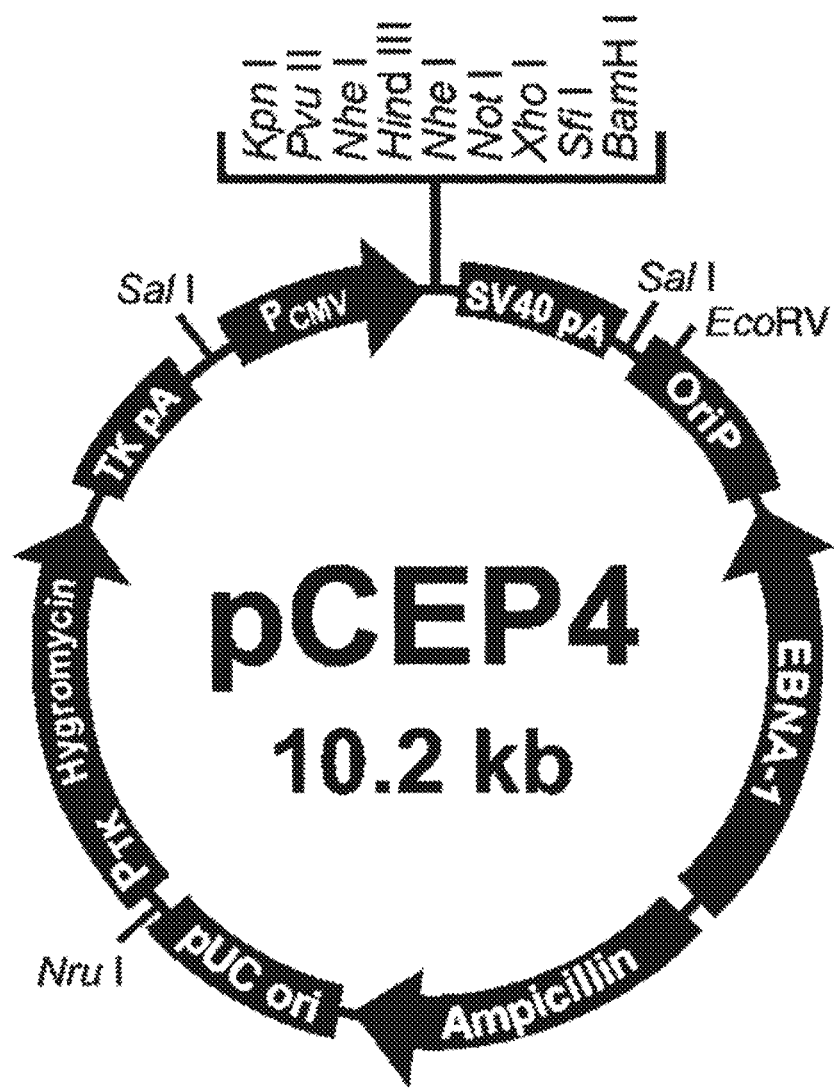
FIG. 1. Expression vector and system for pro.BMP9 and pro.BMP10.

According to a first aspect of the invention, there is provided a polypeptide selected from bone morphogenetic protein 10 (BMP10), or a bone morphogenetic protein 9 (BMP9) variant lacking osteogenic activity, for use in the treatment of a vascular disease or a respiratory disease.

The present invention is directed to the therapeutic use of bone morphogenetic proteins which maintain endothelial cell signalling activity (for example, as which may be evidenced by the induction of ID1, ID2 and/or BMPR-11 gene expression) but which lack osteogenic activity (for example as which may be measured by alkaline phosphatase (ALP) activity in the mouse myoblast cell line C2012). For example, BMP10 and the BMP9 variants disclosed herein not only maintain endothelial cell signalling activity but are synergistically devoid of osteogenic activity. Thus, native BMP10 and the BMP9 variants disclosed herein represent a more desirable agonist than native BMP9 for treating a vascular disease or a respiratory disease, in particular PAH by virtue of lacking the ability to promote bone formation.

References herein to "BMP10" and "bone morphogenetic protein 10" refer to a human polypeptide belonging to the TGF-β superfamily of proteins which is encoded by the BMP10 gene (having the sequence shown in SEQ ID NO: 1) and which has the 424 amino acid sequence shown in SEQ ID NO: 2 wherein amino acid residues 1 to 21 comprise the signal peptide, amino acid residues 22 to 316 comprise the propeptide and amino acid residues 317 to 424 comprise mature BMP10.

References herein to "a BMP9 variant" and "bone morphogenetic protein 9 variant" refer to a human polypeptide belonging to the TGF-β superfamily of proteins which is encoded by the BMP9 gene (having the sequence shown in SEQ ID NO: 3) and which has a variant of the 429 amino acid sequence shown in SEQ ID NO: 4 wherein amino acid residues 1 to 22 comprise the signal peptide, amino acid residues 23 to 319 comprise the propeptide and amino acid residues 320 to 429 comprise mature BMP9. For the avoidance of doubt, it should be stressed that such BMP9 variant must maintain endothelial cell signalling activity but lack osteogenic activity.

References to "variant" include a genetic variation in the native, non-mutant or wild type sequence of BMP9. Examples of such genetic variations include mutations selected from: substitutions, deletions, insertions and the like.

References to "lacking osteogenic activity" or "lack osteogenic activity" as used herein refer to a BMP9 variant comprising one or more, mutations of the sequence of SEQ ID NO: 4 which results in elimination, minimisation and/or suppression of osteogenic activity (for example, which may be measured by alkaline phosphatase (ALP) activity in the mouse myoblast cell line C2012). Advantageous BMP9 variants will be those which maintain endothelial specific signaling (i.e. those which have at least 0.75 fold ID1 induction compared to wild type BMP9, as measured by ID1 gene expression in HMEC-1 cells) and which have a lower value of osteogenic activity (i.e. less than 0.5 fold compared to wild type BMP9, as measured by ALP activity in the mouse myoblast cell line C2C12).

More desirable BMP9 variants will be those which maintain endothelial specific signaling (i.e. those which have at least 0.75 fold ID1 induction compared to wild type BMP9, as measured by ID1 gene expression in HMEC-1 cells) and negligible osteogenic activity (i.e. less than 0.1 fold compared to wild type BMP9, as measured by ALP activity in the mouse myoblast cell line C2012).

Most desirable BMP9 variants will be those which have increased endothelial specific signaling (i.e. those which have higher levels of ID1 induction compared to wild type BMP9, as measured by ID1 gene expression in HMEC-1 cells) and negligible osteogenic activity (i.e. less than 0.1 fold compared to wild type BMP9, as measured by ALP activity in the mouse myoblast cell line C2C12).

In one embodiment, the vascular disease is selected from: pulmonary hypertension; pulmonary arterial hypertension; hereditary haemorrhagic telangiectasia; atherosclerosis; and hepatopulmonary syndrome.

In a further embodiment; the vascular disease is selected from: pulmonary hypertension; pulmonary arterial hypertension; hereditary haemorrhagic telangiectasia; and hepatopulmonary syndrome.

In a further embodiment, the vascular disease is selected from pulmonary arterial hypertension.

In one embodiment, the respiratory disease is selected from: obstructive lung diseases such as chronic obstructive pulmonary disease (COPD), chronic bronchitis and emphysema; pulmonary vascular diseases such as pulmonary edema and pulmonary hemorrhage; respiratory failure and respiratory distress syndrome, such as acute lung injury and acute respiratory distress syndrome; and interstitial lung diseases, such as idopathic pulmonary fibrosis.

In one embodiment, the polypeptide is BMP10. Thus, according to a further aspect of the invention there is provided BMP10 for use in the treatment of a vascular disease or a respiratory disease. Data is provided herein which shows that BMP10 is as potent as BMP9 in inducing ID1, ID2 and BMPR-II gene expression (see FIGS. 3A to 3C). Furthermore, BMP10 has been shown herein to exhibit the same anti-apoptotic activity as BMP9 in protecting hPAECs against TNFα-CHX induced apoptosis (see FIG. 3D). Crucially, however, BMP10 did not induce any ALP activity at the highest concentration tested (see FIG. 3F) unlike BMP9.

In a further embodiment, the polypeptide is BMP10 comprising the amino acid sequence of SEQ ID NO: 2.

In a further embodiment, the polypeptide is BMP10 encoded by the nucleotide sequence of SEQ ID NO: 1.

In a further embodiment, the polypeptide is the prodomain bound form of BMP10 (pro.BMP10). Data is provided herein which demonstrates that the pro.BMP10 complex is very stable (see FIGS. 4B and 4C) and is likely to be the preferred form for the treatment of vascular and respiratory diseases, such as PAH.

In a further embodiment, the pro.BMP10 comprises a propeptide sequence having the amino acid sequence of residues 22-316 of SEQ ID NO: 2 non-covalently bound to a mature BMP10 sequence having the amino acid sequence of residues 317-424 of SEQ ID NO: 2.

In a further embodiment, the pro.BMP10 comprises a tetramer containing two of said propeptide sequences and two of said mature BMP10 sequences.

In one embodiment, the polypeptide is a BMP9 variant lacking osteogenic activity. Thus, according to a further aspect of the invention there is provided a BMP9 variant lacking osteogenic activity for use in the treatment of a vascular disease or a respiratory disease.

In a further embodiment, the polypeptide is a variant of the prodomain bound form of BMP9 (pro. BMP9).

In a further embodiment, the variant of pro.BMP9 comprises a variant of: the propeptide sequence having the amino acid sequence of residues 23-319 of SEQ ID NO: 4 non-covalently bound to a mature BMP9 sequence having the amino acid sequence of residues 320-429 of SEQ ID NO: 4.

In a further embodiment, the variant of pro.BMP9 comprises a tetramer containing two of said propeptide sequences and two of said mature BMP9 sequences:

In one embodiment, the BMP9 variant lacking osteogenic activity comprises a substitution, deletion or insertion mutant of the amino acid sequence of SEQ ID NO: 4.

In a further embodiment, the BMP9 variant lacking osteogenic activity comprises a substitution mutant of the amino acid sequence of SEQ ID NO: 4.

In a further embodiment, the substitution mutant of the amino acid sequence of SEQ ID NO: 4 comprises one or more (i.e. single, double, triple mutants etc.) of the following substitutions: H326A, D342A, S343A, W344A, I346A, K349A, F362A, D366A, K372A, I375A, L379A, H381A, L382A, K383A, K390A, S402A, L404A, K406A, D408A, V411A, T413A, L414A, Y416A and Y418A.

In a further embodiment, the BMP9 variant lacking osteogenic activity is selected from one of the following BMP9 variants of SEQ ID NO: 4: H326A, D342A, S343A, W344A, I346A, K349A, F362A. D366A, K372A, I375A, L379A, H381A, L382A, K383A, K390A, S402A, L404A, K406A, D408A, V411A, T413A, L414A, Y416A and Y418A.

In a further embodiment, the substitution mutant of the amino acid sequence of SEQ ID NO: 4 comprises one or more (i.e. single, double, triple mutants etc.) of the following substitutions: H326A, S343A, K349A, F362A, D366A, I375A, L379A, L382A, K390A, S402A, D408A, Y416A and Y418A.

Figure 5:
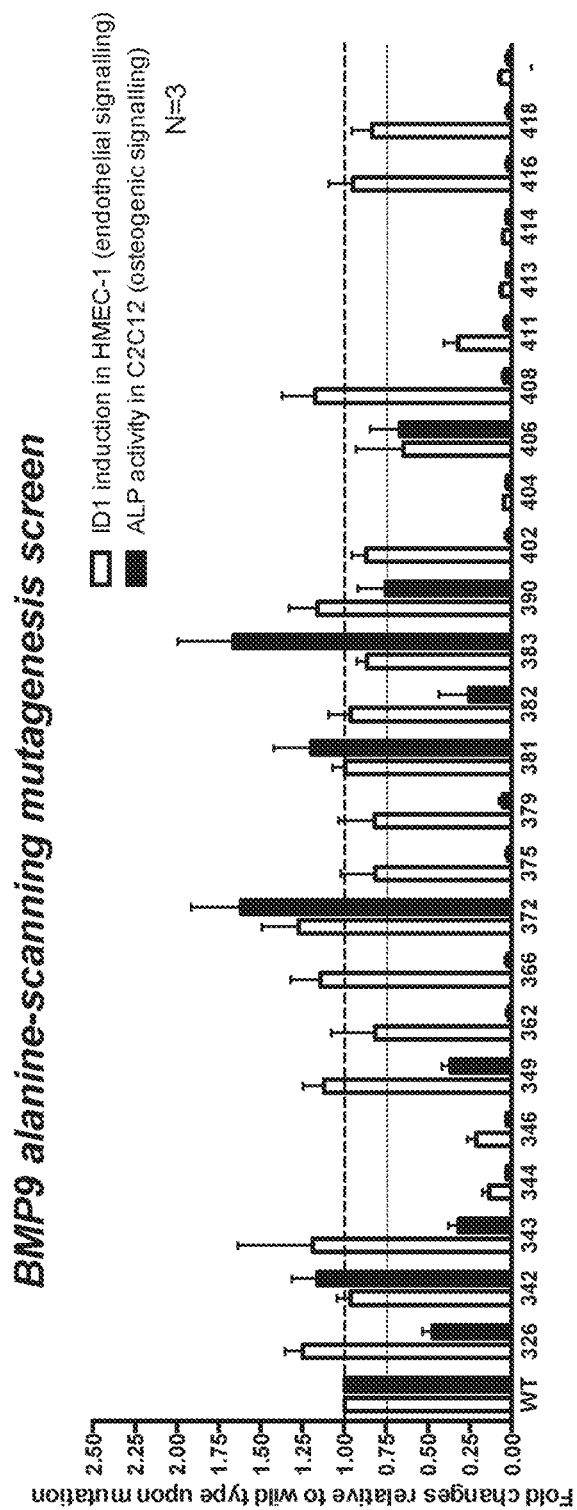
FIG. 5. Summary of BMP9 alanine scanning mutagenesis. Twenty-four BMP9 variants were generated and tested in both HMEC-1 cells for ID1 gene induction and C2C12 cells for alkaline phosphatase activity. All results were normalized to wild type (WT) BMP9 and average of three experiments are shown, denotes untreated cells.

In a further embodiment, the BMP9 variant lacking osteogenic activity is selected from one of the following BMP9 variants of SEQ ID NO: 4: H326A, S343A, K349A, F362A, D366A, I375A, L379A, L382A, K390A, S402A, D408A, Y416A and Y418A. Data is provided herein which demonstrates that these mutant sequences maintain the beneficial effect of endothelial specific signaling and having greatly reduced osteogenic signaling (as evidenced by at least 0.75 fold ID1 induction and less than 0.5 fold ALP activity when compared to wild type BMP9 in FIG. 5).

In a further embodiment, the substitution mutant of the amino acid sequence of SEQ ID NO: 4 comprises one or more (i.e. single, double, triple mutants etc.) of the following substitutions: F362A, D366A, I375A, L379A, S402A, D408A, Y416A and Y418A.

In a further embodiment, the BMP9 variant lacking osteogenic activity is selected from one of the following BMP9 variants of SEQ ID NO: 4: F362A, D366A, I375A, L379A, S402A, D408A, Y416A and Y418A. Data is provided herein which demonstrates that these mutant sequences maintain the beneficial effect of endothelial specific signaling but lack osteogenic signaling (as evidenced by at least 0.75 fold ID1 induction and negligible (i.e. less than 0.1 fold) ALP activity when compared to wild type BMP9 in FIG. 5).

In a further embodiment, the substitution mutant of the amino acid sequence of SEQ ID NO: 4 comprises one or both (i.e. a single or double mutant) of the following substitutions: D366A or D408A.

In a further embodiment, the BMP9 variant lacking osteogenic activity is selected from one of the following BMP9 variants of SEQ ID NO: 4: D366A or D408A. Data is provided herein which demonstrates that these mutant sequences maintain the beneficial effect of BMP9 but are not able to initiate the osteogenic signaling and hence remove the potential risk of bone formation by administration of BMP9 in vivo (see the results shown in FIGS. 2A-2D). Data is also provided herein which demonstrates that these mutant sequences have increased endothelial specific signaling but lack osteogenic signaling (as evidenced by a greater than 1 fold ID1 induction and negligible (i.e. less than 0.1 fold) ALP activity when compared to wild type BMP9 in FIG. 5).

In a further embodiment, the BMP9 variant lacking osteogenic activity is selected from a D408A BMP9 variant of SEQ ID NO: 4. Data is provided herein which demonstrates that this mutant sequence has been shown to be able to rescue PAEC early apoptosis induced by tumor necrosis factor α (TNFα) and cycloheximide (CHX) (see the results shown in FIG. 7).

In a further embodiment, the BMP9 variant lacking osteogenic activity is selected from a D366A BMP9 variant comprising the amino acid sequence of SEQ ID NO: 5 or a D408A BMP9 variant comprising the amino acid sequence of SEQ ID NO: 6.

It will be appreciated that the BMP9 variants disclosed herein constitute previously unknown polypeptides which therefore form novel aspects of the invention. Thus, according to a further aspect of the invention there is provided a BMP9 variant comprising the amino acid sequence of SEQ ID NO: 5. According to a further aspect of the invention there is provided a BMP9 variant comprising the amino acid sequence of SEQ ID NO: 6.

While it is possible for the active polypeptide to be administered alone, it is preferable to present it as a pharmaceutical composition (e.g. formulation). In one embodiment this is a sterile pharmaceutical composition.

The invention further provides pharmaceutical compositions, as defined above, and methods of making a pharmaceutical composition comprising (e.g admixing) at least one polypeptide of the invention together with one or more pharmaceutically acceptable excipients and optionally other therapeutic or prophylactic agents.

Thus, according to a further aspect of the invention there is provided a pharmaceutical composition comprising BMP10, or a BMP9 variant lacking osteogenic activity, for use in the treatment of a vascular disease or a respiratory disease.

According to a further aspect of the invention there is provided a pharmaceutical composition comprising the BMP9 variants as defined herein, such as the D366A BMP9 variant comprising the amino acid sequence of SEQ ID NO: 5 or the D408A BMP9 variant comprising the amino acid sequence of SEQ ID NO: 6.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing the polypeptides of the invention can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21 (2) 2004, p 201-230).

It will be appreciated that gene therapy comprising the BMP10 or BMP9 variant of the invention is within the scope of the invention. For example, a vector encoding the BMP10 or BMP9 variant nucleotide sequence is administered to the host human subject resulting in endogenous expression (such as endogenous expression in the liver) of the BMP10 or BMP9 variant polypeptide for release into the circulation. Thus, according to a further aspect of the invention there is provided a vector comprising a nucleotide sequence encoding BMP10 or a BMP9 variant for use in the treatment of a vascular disease or a respiratory disease. In a further embodiment, the vector comprises the nucleotide sequence of SEQ ID NO: 1.

In one embodiment, the vector is a viral vector. In a further embodiment, the viral vector is selected from a: retrovirus, adenovirus, lentivirus, herpes simplex, vaccinia and adeno-associated virus. In a further embodiment, the vector is a viral vector is an adeno-associated virus.

In an alternative embodiment, the vector is a non-viral vector. The use of non-viral vectors has a number of advantages over the use of viral vectors, such as ease of large scale production and low immunogenicity in the host. Examples of non-viral gene therapy methods include: injection of naked DNA, electroporation, gene gun, sonoporation, magnetofection and the use of oligonucleotides, lipoplexes, dendrimers, and inorganic nanoparticles.

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use.

The pharmaceutical formulation can be prepared by lyophilising a polypeptide of the invention. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one particular embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another particular embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active polypeptide together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract. Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the polypeptide in the stomach or in the ileum, duodenum, jejenum or colon.

Instead of, or in addition to, a coating, the drug can be presented in a solid matrix comprising a release controlling agent, for example a release delaying agent which may be adapted to release the polypeptide in a controlled manner in the gastrointestinal tract. Alternatively the drug can be presented in a polymer coating e.g, a polymethacrylate polymer coating, which may be adapted to selectively release the polypeptide under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active polypeptide can be formulated in a delivery system that provides osmotic control of the release of the polypeptide. Osmotic release and other delayed release or sustained release formulations (for example formulations based on ion exchange resins) may be prepared in accordance with methods well known to those skilled in the art.

The polypeptides of the invention may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Particularly, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, particularly from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The polypeptides of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active polypeptide. Solutions of the active polypeptide may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active polypeptide together with an inert solid powdered diluent such as lactose:

The polypeptides of the invention will generally be presented in unit dosage form and, as such, will typically contain sufficient polypeptide to provide a desired level of biological activity. For example, a formulation may contain from 1 nanogram to 2 grams of active ingredient, e.g. from 1 nanogram to 2 milligrams of active ingredient. Within these ranges, particular sub-ranges of polypeptide are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active polypeptide.

The active polypeptide will be administered to a patient in need thereof (for example a human or animal patient) in an amount sufficient to achieve the desired therapeutic effect.

According to a further aspect of the invention, there is provided a method of treating a vascular disease or a respiratory disease which comprises administering to a subject in need thereof a therapeutically effective amount of a polypeptide selected from bone morphogenetic protein 10 (BMP10), or a bone morphogenetic protein 9 (BMP9) variant lacking osteogenic activity.

The following studies illustrate the invention:

Abbreviations

ActR-IIA(B); activin receptor typed IA(B);
ALK1, 2, 3, 6: activin receptor-like kinase 1, 2, 3, 6;
ALP: alkaline phosphatase;
BMP: bone morphogenetic protein;
BMPR-II; bone morphogenetic protein receptor type II;
ECD: extracellular domain;
FBS: fetal bovine serum:
HMEC-1: human microvascular endothelial cells;
hPAEC: human pulmonary artery endothelial cells;
MSC: mesenchymal stem cells;
PAH: pulmonary arterial hypertension;
pro.BMP9; prodomain bound BMP9;
pro.BMP10: prodomain bound BMP10; and
gPCR: quantitative PCR.

Materials and Methods

Generating Recombinant Human Pro. BMP9 and Pro.BMP10

The full-length cDNA containing open reading frame of human pre-pro-BMP9 was cloned into the expression vector pCEP4 between HindIII and XhoI sites (see FIG. 1). Similarly, the full-length cDNA of human pre-pro-BMP10 was cloned into the expression vector pCEP4 between XhoI and BamHI sites (see FIG. 1). The inserts were verified by DNA sequencing. Pro.BMP9 variants were generated using the QuickChange Site-Directed Mutagenesis kit (Stratagene) and all mutations were verified by DNA sequencing.

Plasmids containing pre-pro-BMP9 (or pre-pro-BMP10) were transfected into HEK-EBNA cells using polyethylenimine in DMEM medium containing 5% fetal bovine serum (FBS). Plasmids expressing human furin were co-transfected to facilitate the processing of pro-BMP9 and pro-BMP10. Cells were changed into CDCHO medium without serum the following day and conditioned media were harvested after 3-4 days. The identities of pro.BMP9 and pro.BMP10 in the conditioned media were confirmed by Western blotting using anti-BMP9 (MAB3209, R&D Systems), anti-BMP9 prodomain (AF3879, R&D Systems) or anti-BMP10 (MAB2926, R&D Systems) antibodies, respectively.

To purify pro.BMP10, 1-5 litres of conditioned media were loaded onto a Q-Sepharose column pre-equilibrated in 50 mM Tris.HCl, pH7.4, 50 mM NaCl. Bound proteins were eluted with a NaCl gradient (50-2000 mM). Fractions were analysed by a non-reducing SDS-PAGE and those containing pro.BMP10 were pooled and concentrated before loading onto an 5200 gel filtration column. Pro.BMP10 from the 5200 column was over 90% pure and the identities of BMP10 prodomain and mature BMP10 were further confirmed by in-gel digestion and mass spectrometric identifications.

Signalling Assays by Quantitative PCR (qPCR) and Smad1/5/8 Phosphorylation in Endothelial Cells For the signalling assays, the concentration of pro.BMP9 was determined by ELISA using R&D BMP9 as standards; and the concentration of pro.BMP10 was quantified by western blot and ImageJ using R&D BMP10 as standards.

After serum-starvation, HMEC-1 cells were treated with BMP ligands at indicated concentrations. 8 hours after treatment, mRNA was extracted and the expression levels of ID1, 02 or BMPR-11 were measured by quantitative PCR, I32-microglobulin was used as control and fold changes relative to non-treated samples were plotted. Mean±SEM is shown, N=2. For Smad1/5/8 phosphorylation assay, serum-starved HMEC-1 cells were treated with BMP ligands at indicated concentrations for 1 hour and the signalling was stopped by placing the dishes on dry ice. Lysis buffer (125 mM Tris.HCl, pH6.8, 2% SDS and 10% glycerol) was added and the protein concentration in the total cell lysate was determined using DC™ protein Assay (Bio-Rad). 25-35 µg of total cell protein was used for immunoblotting and the phosphorylation of Smad1/5/8 was monitored by anti-pSmad1/5/8 antibody (Cell Signaling, cat No, 9516). α-tubulin was used as a loading control.

Alkaline phosphatase (ALP) activity in mouse myoblast cell line C2C12

C2C12 cells were seeded at 20,000 cells/well in 24-well plate in DMEM with 10% FBS. After 48 hours, cells were quiesced with DMEM containing 0.25% FBS for 16 hours and treated with BMP ligands at indicated concentrations for 64 hours. Cells were lysed in 1% Triton X-100/PBS and the total protein concentration in the cell lysate was determined using DC™ protein Assay (Bio-Rad). ALP activity in the cell lysate was measured using the chromogenic phosphatase substrate 4-nitrophenyl phosphate disodium salt (Sigma, S0942) and the soluble product was measured at 405 nm on a plate reader. In all assays, control BMP9 and BMP10 were purchased from R&D Systems.

Results

BMP9 Signalling and Data Supporting its Therapeutic Potential in PAH

BMP9 and BMP10 were identified as the ligands for the orphan receptor ALK1 (David et al (2007) Blood 109(5): 1953-1961). In endothelial cells, they induce a similar set of genes, including ID1, ID2 and BMPRII. BMP9 is synthesised in the liver (Miller et al (2000) J. Biol. Chem. 275(24):17937-17945; Bidart et al (2012) Cell. Mol. Life Sci. 69(2):313-324), circulates at 2-10 ng/ml and is the only confirmed BMP circulating at active concentrations (Herrera and Inman (2009) BMC Cell Biol. 10:20; David et al (2008) Circ. Res. 102(8):914-922). BMP9 is a vascular quiescence factor, inhibiting EC migration, proliferation and angiogenesis in vitro, thus promoting vascular stability (David et al (2008), supra).

Engineering of BMP9 Variants that Retain Endothelial Protective Properties but that are Devoid of Bone Forming Activity Despite the potential for treating cardiovascular diseases through selective activation of endothelial receptors, BMP9 can also signal in mesenchymal stem cells (MSC) and C2C12 myoblasts. Among 14 BMPs tested, BMP9 was found to have the highest osteogenic signalling in vitro and bone-formation activity in vivo (Kang et al (2004) Gene Ther. 11(17):1312-1320; Luther et al (2011) Curr. Gene Ther. 11(3):229-240). Both ALK1 and ALK2 are required for the osteogenic activity of BMP9 (Luo et al (2010) J. Biol. Chem. 285(38):29588-29598), but the nature of the interaction of BMP9 with ALK1 and ALK2 in the context of osteogenic activity is not known. Although ALK2 is also expressed by vascular endothelial cells (Upton et al (2008) Mol. Pharmacol. 73(2):539-552), ALK1 is the major type I receptor mediating BMP9 responses in these cells (Upton et al (2009) J. Biol. Chem. 284(23):15794-15804; Scharpfenecker et al (2007) J. Cell Sci. 120 (Pt 6):964-972). The type II receptor requirement for BMP9-osteogenic activity has been investigated in MSCs. It has been shown that expression of dominant negative mutants of all three type II BMP receptors, BMPR-II, ActR-IIA and ActR-IIB, can inhibit BMP9-induced osteogenic activity, with dominant negative ActR-IIB being the most potent (Wu et al (2010) Acta biochimica et biophysica Sinica 42(10):699-708).

Figure 2A:
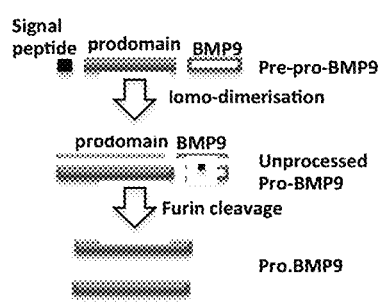
FIGS. 2A-2D. Generation of non-osteogenic BMP9 variants. A. Schematic drawing of BMP9 synthesis and post-translational processing. B-D, Two BMP9 variants (D366A and D408A) have comparable signaling activity as the wild type in endothelial cells in inducing ID1 and ID2 expression (B&C), but lack osteogenic signaling activity in the C2C12 cells (D).
Figure 2B:
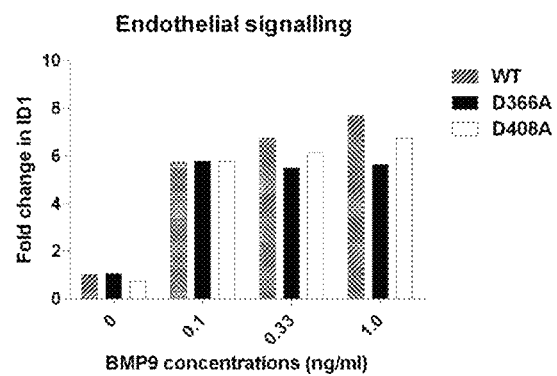
Figure 2C:
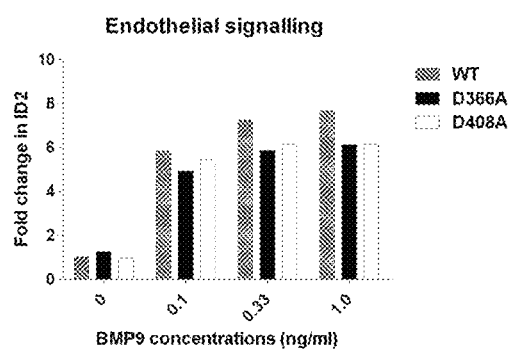
Figure 2D:
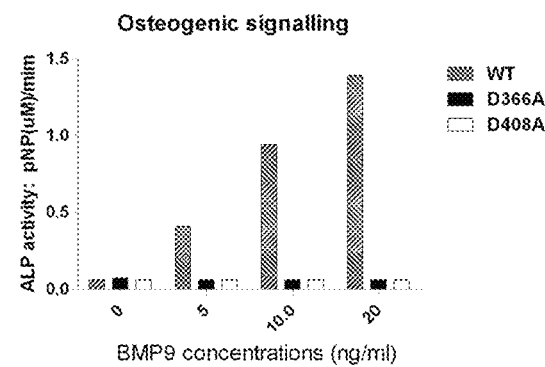

The inventors have hypothesized that by mutating the type I and type II receptor binding sites on BMP9, BMP9 variants can be generated that retain ALK1 binding but lose ALK2 binding. Such BMP9 variants are likely to retain endothelial protective function but lack osteogenic activity. The inventors have already identified two such BMP9 variants that maintain endothelial cell signalling activity, as evidenced by the induction of ID1 and ID2 gene expression, but lack osteogenic signalling activity, assessed by the alkaline phosphatase assay in the C2C12 cells (FIG. 2D).

These BMP9 variants (D366A and D408A) are likely to maintain the beneficial effect in vivo, since they have normal signalling activity in endothelial cells, but they will not be able to initiate the osteogenic signalling and hence remove the potential risk of bone formation by administration of BMP9 in vivo.

BMP9 Alanine Scanning Mutagenesis

Twenty four BMP9 alanine variants (H326A, D342A, S343A, W344A, I346A, K349A, F362A, D366A, K372A, I375A, L379A, H381A, L382A, K383A, K390A, 8402A, L404A, K406A, D408A, V411A, T413A, L414A, Y416A and Y418A) were generated and tested in both HMEC-1 cells for ID1 gene induction and C2C12 cells for alkaline phosphatase activity. The results of this study are summarized in FIG. 5 where it can be seen that thirteen BMP9 variants (H326A, S343A, K349A, F362A, D366A, I375A, L379A, L382A, K390A, 3402A, D408A, Y416A and Y418A) were identified as maintaining the beneficial effect of endothelial specific signaling and having greatly reduced osteogenic signaling (as evidenced by at least 0.75 fold ID1 induction and less than 0.5 fold ALP activity when compared to wild type BMP9). In addition, the results shown in FIG. 5 demonstrate that eight BMP9 variants (F362A, D366A, I375A, L379A, S402A, D408A, Y416A and Y418A) were identified as maintaining endothelial specific signaling but lacking osteogenic signaling (as evidenced by at least 0.75 fold ID1 induction and negligible (i.e. less than 0.1 fold) ALP activity when compared to wild type BMP9). Furthermore, the results shown in FIG. 5 demonstrate that two BMP9 variants (D366A or D408A) increased endothelial specific signaling but lack osteogenic signaling (as evidenced by a greater than 1 fold ID1 induction and negligible (i.e. less than 0.1 fold) ALP activity when compared to wild type BMP9).

Validation of BMP9 Variants in Primary Endothelial Cells

Figure 6:
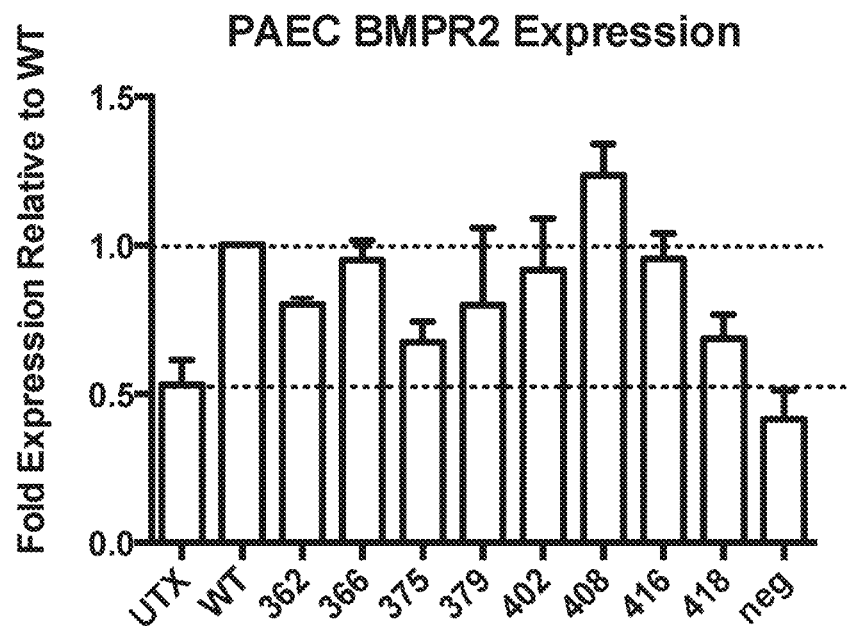
FIG. 6. BMP variants can induce BMPR2 gene expression in hPAECs.
Figure 7:
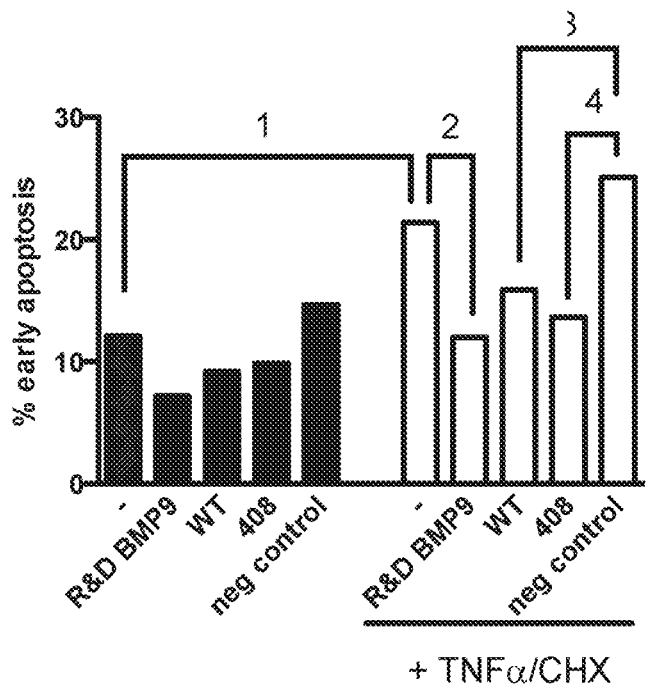
FIG. 7. BMP D408A variant can rescue TNFa/CHX induced early apoptosis in hPAECs.

The eight BMP9 variants (F362A, D366A, I375A, L379A, S402A, D408A, Y416A and Y418A) which were identified above as maintaining endothelial specific signaling but lacking osteogenic signaling were further validated in primary endothelial cells. These mutants were all found to induce BMPR2 gene expression in human pulmonary arterial endothelial cells (hPAECs, FIG. 6). At least one variant, D408A, has been shown to be able to rescue PAEC early apoptosis induced by tumor necrosis factor α (TNFα) and cycloheximide (CHX) (FIG. 7).

BMP10 Signalling in Endothelium

BMP10 is indispensable for heart development (Neuhaus et al (1999) Mech. Dev. 80(2):181-184). BMP10-null mice are embryonic lethal due to severely impaired cardiac development (Chen H et al (2004) Development 131(9):2219-2231), BMP10 regulates cardiac ventricular wall development through the transcription factor Tbx20 (Zhang et al (2011) J. Biol. Chem. 286(42):36820-36829) and overexpression of BMP10 in myocardium disrupts cardiac postnatal hypertrophic growth (Chen et al (2006) J. Biol. Chem. 281(37):27481-27491). In the adult, BMP10 is only expressed in the right atrium (Chen et al (2004) supra). It has been shown that circulating BMP10 mediates flow-dependent arterial quiescence (Laux et al (2013) Development 140(16):3403-3412).

The circulating level of BMP10 is controversial. While BMP10 protein has been detected in human sera using proteomic approaches (Souza et al (2008) Mol. Endocrinol. 22(12):2689-2702) and can be measured by ELISA (Ricard et al (2012) Blood 119(25):6162-6171), other studies using activity assays could not detect circulating BMP10 (Bidart et al (2012) and Herrera and Inman (2009), supra). However, a recent report has demonstrated BMP10 activity in the circulation (Chen et al (2013) Proc. Natl. Acad. Sci. U.S.A. 110(29):11887-11892). Such controversy could be due to circulating BMP10 being in active/inactive states, incomplete processing, inhibition by a serum factor, or the different activity assays used in published reports. The prodomain of BMP10 could play a role in this. For example, it has been reported that the prodomain of BMP10, unlike other BMPs, can inhibit BMP10-induced gene expression in C2C12 cells (Sengle et al (2011) J. Biol. Chem. 286(7):5087-5099). In addition, Biacore measurements have shown that BMP10 has higher affinity for ALK1/BMPR-II than BMP9 (Townson et al (2012) J. Biol. Chem. 287(33):27313-27325) and the loss of BMPR-II protein during the onset of PAH will clearly have an impact on BMP10 signalling. Importantly, in vitro and in vivo studies, BMP10 is devoid of osteogenic activity. Thus, native BMP10 represents a more desirable agonist than native BMP9 for treating PAH.

Comparison of BMP9 and BMP10 Activity

Figures 3A, 3B, 3C, 3D, 3E, 3F:
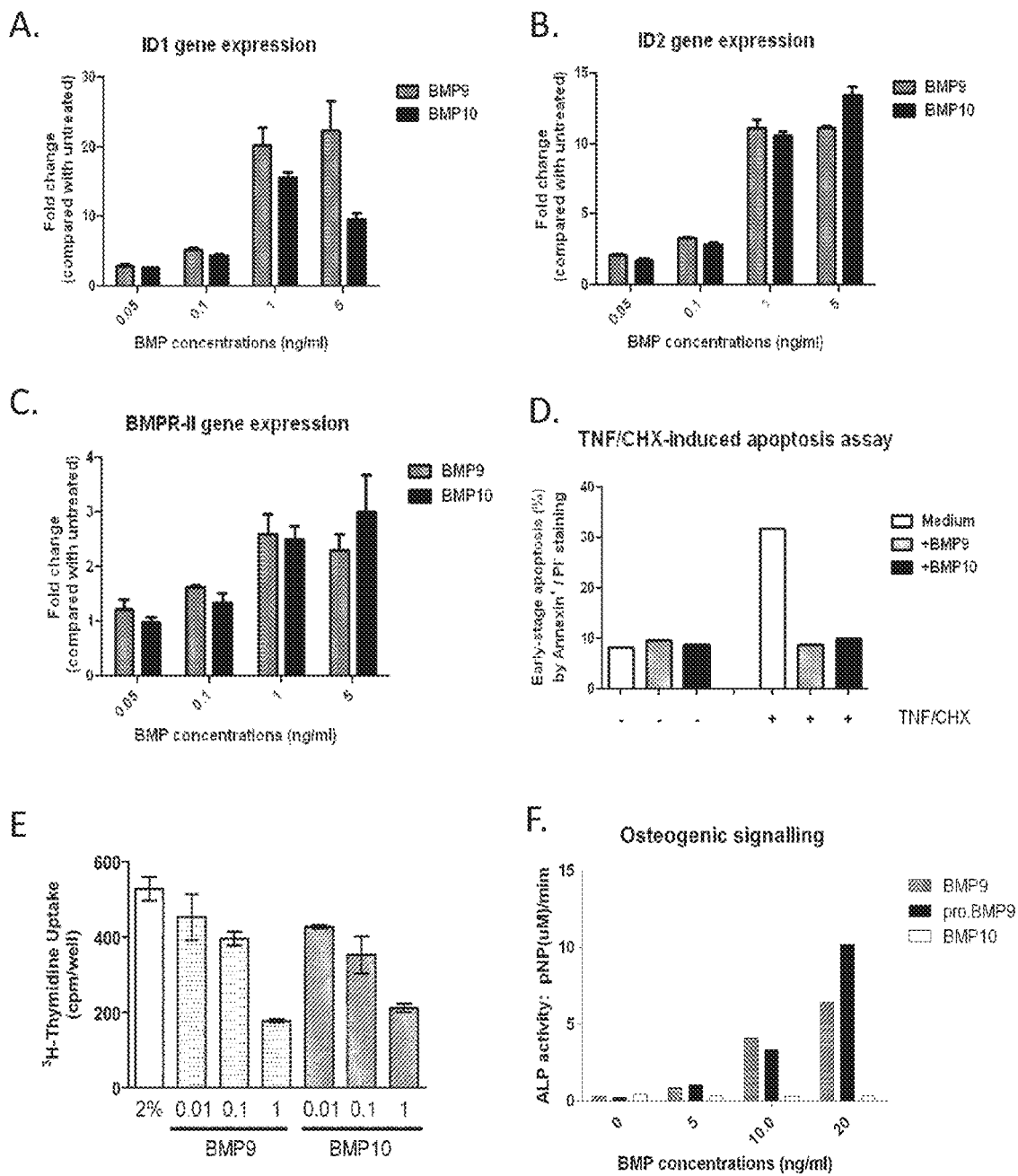
FIGS. 3A-3F, Comparison of endothelial cell signalling activity and C2C12 cell osteogenic activity between BMP9 and BMP10, A-C: BMP9 and BMP10 have similar signalling activity HMEC-1. After serum-starvation, HMEC-1 cells were treated with BMP9 or BMP10 at indicated concentrations. 8 hours after treatment, mRNA was extracted and the expression levels of ID1, ID2 or BMPR-II were measured by quantitative PCR. 12-microglobulin was used as control and fold changes relative to non-treated samples were plotted, Mean±SEM is shown, N=2; D. Similar to BMP9, BMP10 can also protect hPAEC against TNFα-CHX induced apoptosis. Methods are as FIG. 3A, N=1; E. BMP9 and BMP10 inhibit endothelial cell proliferation to similar extents. HPAECs were treated with BMP9 or BMP10 (both R&D Systems) in EBM2/2% FBS for 24 hours. Cells were incubated with 0.5 μCi/well $^3$H-Thymidine for the final 6 hours. Cells were then lysed and $^3$H-Thymidine uptake measured by liquid scintillation counting. N=1 experiment, mean±SEM of 4 wells. F. Unlike BMP9, BMP10 has no detectable osteogenic activity measured as ALP activity in C2C12 cells. C2C12 cells were treated with BMP9 or BMP10 at indicated concentrations for 64 hours. Cells were lysed in 1% Triton X-100/PBS and ALP activity in the cell lysate was measured using the chromogenic phosphatase substrate 4-nitrophenyl phosphate disodium salt (Sigma, S0942) and the soluble product was measured at 405 nm on a plate reader. In all assays, both BMP9 and BMP10 were purchased from R&D Systems. Pro.BMP9 was produced in-house and its concentration (mature ligand) was determined by ELISA, using BMP9 from R&D system as standard.

A concentration-response signalling assay in human microvascular endothelial cells (HMEC-1) showed that BMP10 is as potent as BMP9 in inducing ID1, ID2 and BMPR-II gene expression (FIGS. 3A to 3C). Importantly, BMP10 exhibits the same anti-apoptotic activity as BMP9 in protecting hPAECs against TNFα-CHX induced apoptosis (FIG. 3D). BMP9 is reported to maintain the stability of the vasculature by suppressing endothelial cell proliferation (David et al (2008) supra). Both BMP9 and BMP10 repress DNA synthesis to similar extents, measured as $^3$H-thymidine uptake, in hPAECs (FIG. 3E). Alkaline phosphatase (ALP) is a key enzyme in the osteogenic pathway and BMP9-induced ALP activity can be detected in C2C12 cells at 5 ng/ml BMP9. However, under identical conditions, BMP10 did not induce any ALP activity at the highest concentration tested (20 ng/ml, FIG. 3F), consistent with the previous study using the adenovirus-expressed BMPs in C2C12 cells (Kang et al (2004) supra).

Figures 4A, 4B, 4C, 4D, 4E:
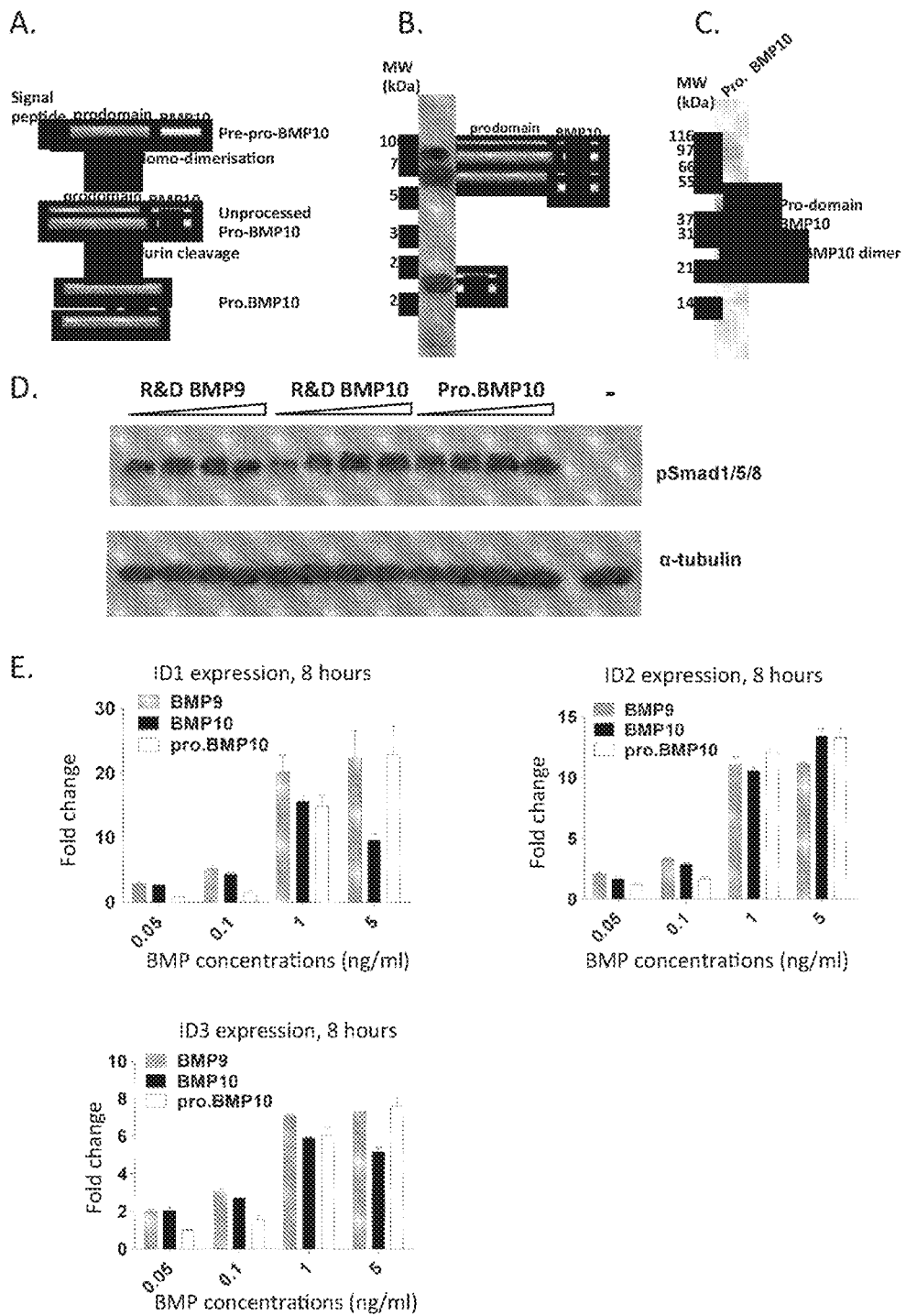
FIGS. 4A-4E. In-house generated pro.BMP10 is fully active. A. Schematic drawing of BMP10 synthesis and post-translational processing. B. BMP10 expressing conditioned medium, blotted by anti-BMP10 antibody (R&D Systems), C. Non-reducing SDS-PAGE showing the purification of pro.BMP10 from an S200 gel filtration column. The identities of prodomain and BMP10 have been verified by western blot and mass spec peptide mapping. D&E. Comparing pro.BMP10 signalling capacity with BMP9 and BMP10 (from R&D Systems) in HMEC-1, by monitoring Smad1/5/8 phosphorylation and ID1/2/3 gene expression, Methods are as in FIGS. 3A to 3C, BMP concentrations in D. are 0.05, 0.1, 1, 5 ng/ml and treatment time is 1 hour. Mean±SEM is shown, N=2.

Potential of Administration of BMP10 and Prodomain Bound BMP10 for Treating PAH and Other Cardiovascular Diseases BMPs are synthesized as pre-pro-proteins and the prodomain is cleaved upon secretion (FIG. 4A). A previous report showed that the prodomain of BMP10 can inhibit BMP10 activity and BMP10 is likely to circulate in an inactive form. The inventors have generated a large quantity of prodomain bound BMP10 (pro.BMP10). In contrast to the previous report, The prodomain was found to remain bound to BMP10 when BMP10 is produced from mammalian cells and that the pro.BMP10 complex is very stable (FIGS. 4B and 4C), This indicates that pro.BMP10 is likely to be the circulating form. Furthermore, the inventors have demonstrated in the HMEC-1 cells (FIGS. 4D and 4E) and hPAEC that pro.BMP10 have comparable activities to BMP9 and BMP10 purchased from a commercial source (R&D Systems). Since the prodomain protects the hydrophobic surface of BMP10 and hence stabilises the circulating form of BMP10, pro.BMP10 is likely to be a preferred form for the in vivo administration for treating PAH and other cardiovascular diseases.

BMP9 and BMP10 Inhibit Blood Outgrowth Endothelial Cell (BOEC) Tube Formation in Collagen Gels Blood outgrowth endothelial cells can be isolated from the peripheral blood of most individuals and represent a highly proliferative cell type that are highly representative of human endothelial cells. It has been shown that, like endothelial cells, BOECs form vacuolised capillary-like structures in a 3-dimensional collagen:fibronectin matrix. The results of this analysis are shown in FIGS. 8B and 8C which not only demonstrates the anti-angiogenic role of BMP9 and BMP10 but also shows that BMP9 as well as being anti-proliferative for endothelial cells, protects endothelial cells from apoptosis, and protects endothelial cells from increased permeability. The inhibition by BMP9 is evident even at low concentrations.

The invention claimed is:

1. A method of treating pulmonary arterial hypertension in a subject comprising administering to the subject a polypeptide which is a bone morphogenetic protein 9 (BMP9) variant having endothelial cell signaling activity and lacking osteogenic activity, wherein the difference between the amino acid sequence of said BMP9 variant and the amino acid sequence of SEQ ID NO: 4 consists of a substitution selected from the group consisting of F362A, D366A, I375A, L379A, 5402A, Y416A and Y418A.

2. The method of claim 1, wherein the difference between the amino acid sequence of said BMP9 variant and the amino acid sequence of SEQ ID NO: 4 consists of the substitution F362A.

3. The method of claim 1, wherein the difference between the amino acid sequence of said BMP9 variant and the amino acid sequence of SEQ ID NO: 4 consists of the substitution D366A.

4. The method of claim 1, wherein the difference between the amino acid sequence of said BMP9 variant and the amino acid sequence of SEQ ID NO: 4 consists of the substitution I375A.

5. The method of claim 1, wherein the difference between the amino acid sequence of said BMP9 variant and the amino acid sequence of SEQ ID NO: 4 consists of the substitution L379A.

6. The method of claim 1, wherein the difference between the amino acid sequence of said BMP9 variant and the amino acid sequence of SEQ ID NO: 4 consists of the substitution 5402A.

7. The method of claim 1, wherein the difference between the amino acid sequence of said BMP9 variant and the amino acid sequence of SEQ ID NO: 4 consists of the substitution Y416A.

8. The method of claim 1, wherein the difference between the amino acid sequence of said BMP9 variant and the amino acid sequence of SEQ ID NO: 4 consists of the substitution Y418A.

* * * * *